United States Patent
Quill et al.

(10) Patent No.: US 10,849,749 B2
(45) Date of Patent: Dec. 1, 2020

(54) HELICAL COIL MITRAL VALVE ANNULOPLASTY SYSTEMS AND METHODS

(71) Applicant: MEDTRONIC, INC., Minneapolis, MN (US)

(72) Inventors: Jason Quill, Forest Lake, MN (US); Cynthia Clague, Minnetonka, MN (US); Michael Green, Forest Lake, MN (US); Alexander J. Hill, Blaine, MN (US); Ana Menk, St. Paul, MN (US); Paul Rothstein, Elk River, MN (US); Georg Bortlein, Paris (FR)

(73) Assignee: MEDTRONIC, INC., Minneapolis, MN (US)

( * ) Notice: Subject to any disclaimer, the term of this patent is extended or adjusted under 35 U.S.C. 154(b) by 218 days.

(21) Appl. No.: 16/034,061

(22) Filed: Jul. 12, 2018

(65) Prior Publication Data

US 2018/0318080 A1     Nov. 8, 2018

Related U.S. Application Data

(62) Division of application No. 14/328,050, filed on Jul. 10, 2014, now Pat. No. 10,028,832.

(Continued)

(51) Int. Cl.
*A61F 2/24*     (2006.01)
*A61B 17/068*     (2006.01)
(Continued)

(52) U.S. Cl.
CPC .......... *A61F 2/2442* (2013.01); *A61B 17/068* (2013.01); *A61B 2017/00243* (2013.01);
(Continued)

(58) Field of Classification Search
None
See application file for complete search history.

(56) References Cited

U.S. PATENT DOCUMENTS 6,419,696 B1 * 7/2002 Ortiz .................... A61F 2/2409
                                                       623/2.37
6,629,534 B1 * 10/2003 St. Goar ............ A61B 18/1492
                                                      128/898

(Continued)

FOREIGN PATENT DOCUMENTS

| WO | 96/40356 A1 | 12/1996 |
| WO | 01/28432 A1 | 4/2001 |
| WO | 2012/087724 A1 | 6/2012 |

OTHER PUBLICATIONS

International Preliminary Report on Patentability dated Jan. 12, 2016 in corresponding International Patent Application No. PCT/US2014/046176.

(Continued)

*Primary Examiner* — Shaun L David
(74) *Attorney, Agent, or Firm* — Medler Ferro Woodhouse & Mills PLLC

(57) ABSTRACT

Systems and methods for modifying a heart valve annulus in a minimally invasive surgical procedure. A helical anchor is provided, having a memory set to a coiled shape or state. The helical anchor is further configured to self-revert from a substantially straight state to the coiled state. The helical anchor is loaded within a needle that constrains the helical anchor to the substantially straight state. The needle is delivered to the valve annulus and inserted into tissue of the annulus. The helical anchor is then deployed from the needle (e.g., the needle is retracted from over the helical anchor). Once deployed, the helical anchor self-transitions toward the coiled shape, cinching engaged tissue of the valve annulus.

10 Claims, 27 Drawing Sheets

Related U.S. Application Data

(60) Provisional application No. 61/844,507, filed on Jul. 10, 2013.

(51) Int. Cl.
*A61B 17/00* (2006.01)
*A61B 17/064* (2006.01)

(52) U.S. Cl.
CPC .............. *A61B 2017/00331* (2013.01); *A61B 2017/00349* (2013.01); *A61B 2017/00783* (2013.01); *A61B 2017/0649* (2013.01); *A61F 2/2412* (2013.01); *A61F 2002/249* (2013.01); *A61F 2230/0091* (2013.01)

(56) References Cited

U.S. PATENT DOCUMENTS

| | | | |
|---|---|---|---|
| 2002/0111636 A1* | 8/2002 | Fleischman | A61B 17/064 606/139 |
| 2004/0138525 A1 | 7/2004 | Saadat et al. | |
| 2004/0225183 A1 | 11/2004 | Michlitsch et al. | |
| 2004/0260317 A1 | 12/2004 | Bloom et al. | |
| 2006/0265056 A1 | 11/2006 | Nguyen et al. | |
| 2007/0244553 A1 | 10/2007 | Rafiee et al. | |
| 2007/0244554 A1 | 10/2007 | Rafiee et al. | |
| 2007/0244555 A1 | 10/2007 | Rafiee et al. | |
| 2007/0244556 A1* | 10/2007 | Rafiee | A61F 2/2451 623/2.11 |
| 2007/0244557 A1* | 10/2007 | Rafiee | A61F 2/2448 623/2.11 |
| 2008/0071361 A1 | 3/2008 | Tuval et al. | |
| 2008/0140189 A1 | 6/2008 | Nguyen et al. | |
| 2008/0154186 A1 | 6/2008 | Appling et al. | |
| 2010/0010538 A1* | 1/2010 | Juravic | A61F 2/2481 606/228 |
| 2011/0004298 A1* | 1/2011 | Lee | A61F 2/2442 623/2.11 |
| 2011/0029071 A1* | 2/2011 | Zlotnick | A61B 17/00234 623/2.11 |
| 2011/0066231 A1* | 3/2011 | Cartledge | A61B 17/068 623/2.11 |
| 2011/0106247 A1* | 5/2011 | Miller | A61B 17/068 623/2.17 |
| 2011/0208297 A1 | 8/2011 | Tuval et al. | |
| 2012/0035722 A1 | 2/2012 | Tuval | |
| 2012/0277853 A1* | 11/2012 | Rothstein | A61F 2/2466 623/2.11 |
| 2012/0283757 A1* | 11/2012 | Miller | A61F 2/2409 606/151 |
| 2014/0379074 A1* | 12/2014 | Spence | A61F 2/2427 623/2.11 |
| 2015/0272586 A1* | 10/2015 | Herman | A61B 17/12009 606/151 |

OTHER PUBLICATIONS

International Search Report dated Nov. 26, 2014 in corresponding International Patent Application No. PCT/US2014/046176.

* cited by examiner

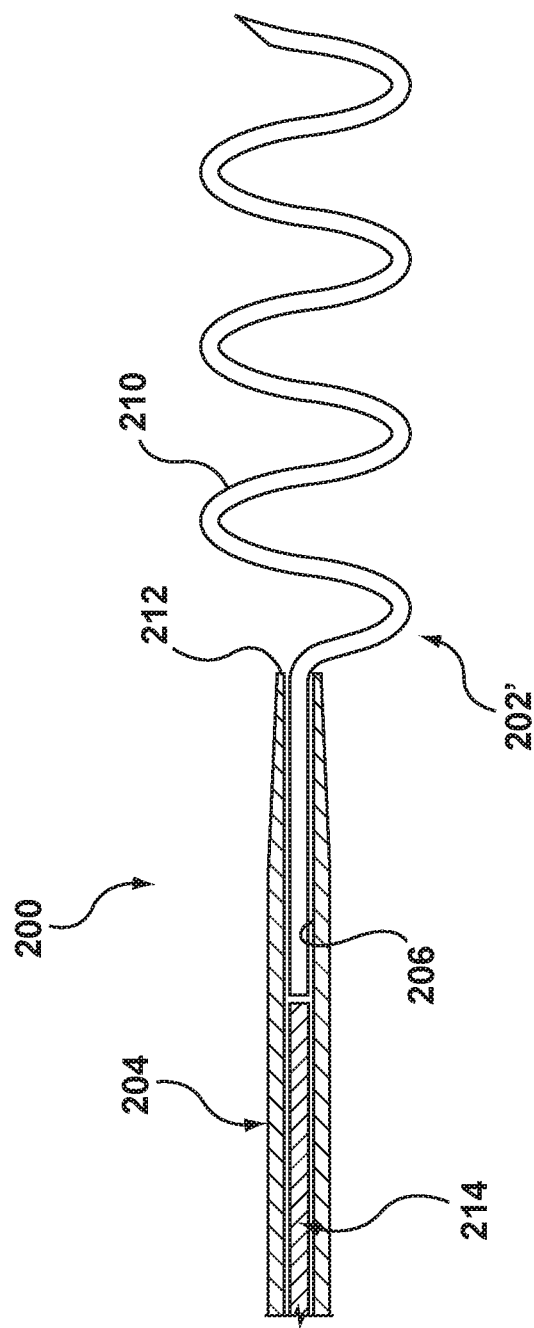

HELICAL COIL MITRAL VALVE ANNULOPLASTY SYSTEMS AND METHODS

CROSS-REFERENCE TO RELATED APPLICATIONS

This application is a divisional of prior U.S. application Ser. No. 14/328,050, filed Jul. 10, 2014, now U.S. Pat. No. 10,028,832, which claims the benefit of U.S. Appl. No. 61/844,507, filed Jul. 10, 2013, each of which is incorporated by reference herein in its entirety.

FIELD OF THE INVENTION

The invention relates generally to the treatment of heart valves. More particularly, it relates to systems, devices, and methods for treating valvular regurgitation, such as mitral regurgitation, via percutaneously delivered helical coils.

BACKGROUND OF THE INVENTION

The heart is a four-chambered pump that moves blood efficiently through the vascular system. Blood enters the heart through the vena cava and flows into the right atrium. From the right atrium, blood flows through the tricuspid valve and into the right ventricle, which then contracts and forces blood through the pulmonic valve and into the lungs. Oxygenated blood returns from the lungs and enters the heart through the left atrium and passes through the mitral valve into the left ventricle. The left ventricle contracts and pumps blood through the aortic valve into the aorta and to the vascular system.

The mitral valve consists of two leaflets (anterior and posterior) attached to a fibrous ring or annulus. In a healthy heart, the mitral valve leaflets close during contraction of the left ventricle and prevent blood from flowing back into the left atrium. Due to various cardiac diseases, however, the mitral valve annulus may become distended, causing the leaflets to remain partially open during ventricular contraction and thus allow regurgitation of blood into the left atrium. This results in reduced ejection volume from the left ventricle, causing the left ventricle to compensate with a larger stroke volume. The increased workload eventually results in dilation and hypertrophy of the left ventricle, further enlarging and distorting the shape of the mitral valve. If left untreated, the condition may result in cardiac insufficiency, ventricular failure, and ultimately death.

It is common medical practice to treat mitral valve regurgitation by either valve repair or replacement. Mitral valve repair includes a variety of procedures to repair or reshape the leaflets to improve closure of the valve during ventricular contraction. If the mitral valve annulus has become distended, a frequent repair procedure involves implanting an annuloplasty ring on the mitral valve annulus. The annuloplasty ring generally has a smaller diameter than the annulus, and when sutured to the annulus the annuloplasty ring draws the annulus into a smaller configuration, bringing the mitral valve leaflets closer together and allowing improved closure during ventricular contraction. Annuloplasty rings may be rigid, flexible or a combination, having both rigid and flexible segments. Rigid annuloplasty rings have the disadvantage of causing the mitral valve annulus to be rigid and unable to flex in response to the contractions of the ventricle, thus inhibiting the normal, three-dimensional movement of the mitral valve that is required for it to function optimally. Flexible annuloplasty rings are frequently made of Dacron® fabric and must be sewn to the annulus tissue with a line of sutures. This eventually leads to scar tissue formation and loss of flexibility and function of the mitral valve. Similarly, combination rings must generally be sutured in place and also cause scar tissue formation and loss of mitral valve flexibility and function. Annuloplasty is normally an open-heart surgical procedure.

Valve replacement also typically entails an open-heart surgical procedure in which the patient's mitral valve is removed and replaced with an artificial valve. One drawback to open-heart surgical techniques is that heart bypass procedures are required to accomplish replacement and/or repair of the valve. Another drawback is that the open-heart procedures require that the patient undergo general anesthesia for a prolonged period of time.

To overcome many of the complications and risks of open-heart surgical procedures, less invasive or minimally invasive surgical techniques have been developed. These procedures can be done on a beating heart and often are performed without general anesthesia or a reduced time under general anesthesia.

More recently, mitral and other cardiac valve annuloplasty devices and procedures have been developed that employ a helical anchor coil in place of the conventional annuloplasty rings (or bands). Examples of such devices and procedures are described, for example, in US Publication Nos. 2007/0244553, 2007/0244554, 2007/0244555, 2007/0244556, and 2007/0244557, each of which is incorporated by reference herein in its entirety. In general terms, one or more helical anchor coils are percutaneously delivered, in a coiled state, to the mitral valve annulus via a tubular delivery member. The helical anchor has a sharpened tip that penetrates into tissue of the valve annulus; as the helical anchor is directed out of the delivery member and rotated along a guide, the helical anchor threads into the annulus tissue. A tether is routed through an inner channel of the so-implanted helical anchor(s) and formed into a loop. The loop is tensioned, effectuating a desired modification in the shape of the valve annulus.

The helical anchor and tether systems described above are quite promising, simulating the surgical placement of an annuloplasty ring on the valve annulus. However, the described minimally invasive delivery techniques may be less than optimal. Further, any improvements in the helical anchor coils and related methods of use will be well-received.

BRIEF SUMMARY OF EMBODIMENTS OF THE INVENTION

Embodiments hereof relate to systems and methods for modifying a heart valve annulus in a minimally invasive surgical procedure. A helical anchor is provided, having a memory set to a coiled shape or state. The helical anchor is further configured to self-revert from a substantially straight state to the coiled state. The helical anchor is loaded within a needle that constrains the helical anchor to the substantially straight state. The needle is delivered to the valve annulus and inserted into tissue of the annulus. The helical anchor is then deployed from the needle (e.g., the needle is retracted from over the helical anchor). Once deployed, the helical anchor self-transitions toward the coiled shape, cinching engaged tissue of the valve annulus.

Other embodiments hereof relate to systems and methods for locating and identifying designated anatomical positions along the valve annulus in a minimally invasive procedure, along with devices, systems and methods for modifying the valve annulus with a helical anchor based upon reference to the identified anatomical positions.

BRIEF DESCRIPTION OF THE DRAWINGS

FIG. 10B is a simplified view of the needle system of FIG. 10A employing another embodiment helical anchor.

DETAILED DESCRIPTION OF EMBODIMENTS OF THE INVENTION

The following detailed description is merely exemplary in nature and is not intended to limit the invention or the application and uses of the invention. Although the description of embodiments hereof is in the context of heart valve annuloplasty, the invention may be adapted to be used for other valve annuloplasty or repair where it is deemed useful. Furthermore, there is no intention to be bound by any expressed or implied theory presented in the preceding technical field, background, brief summary or the following detailed description.

Specific embodiments of the present invention are now described with reference to the figures. The terms "distal" and "proximal" are used in the following description with respect to a position or direction relative to the treating clinician. "Distal" or "distally" are a position distant from or in a direction away from the clinician. "Proximal" and "proximally" are a position near or in a direction toward the clinician.

Figure 1A:
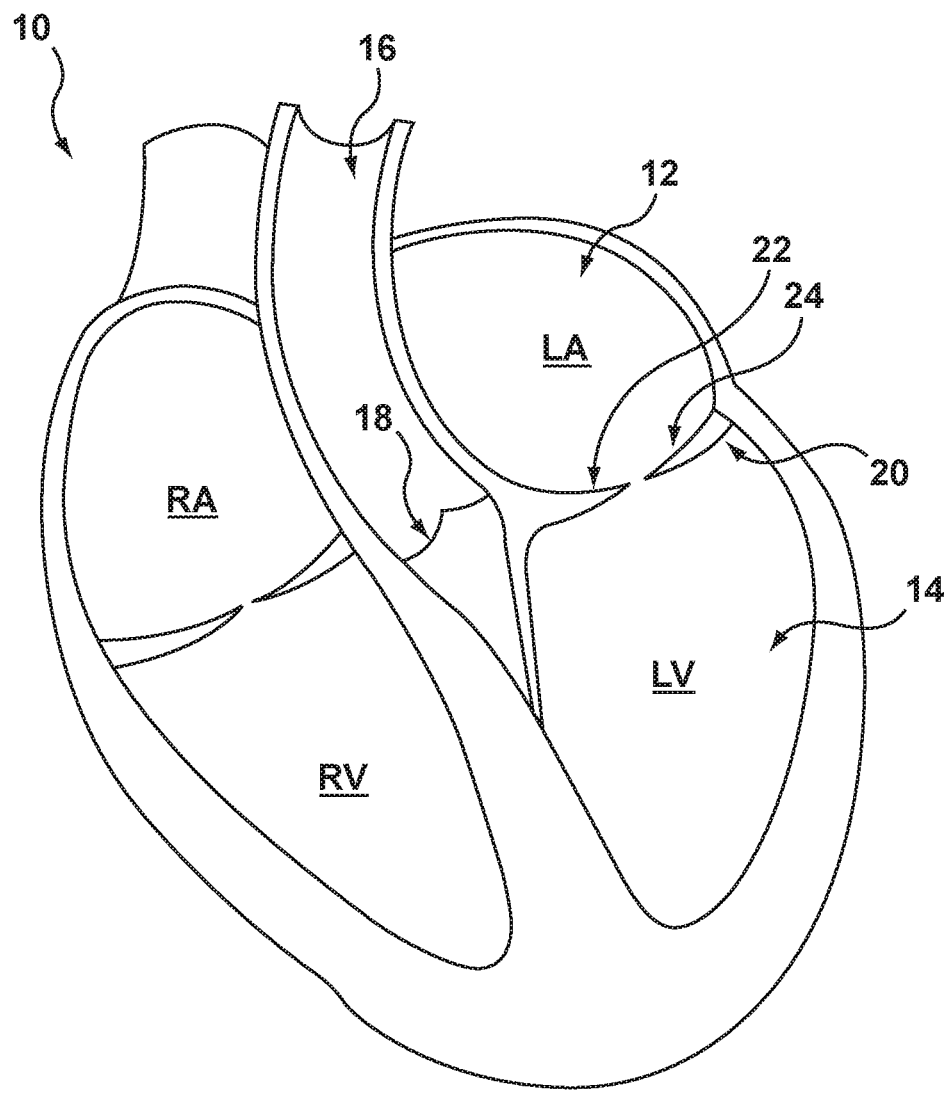
FIG. 1A is a simplified illustration of a heart and illustrating some anatomical features of the mitral valve.

Embodiments in accordance herewith relate to systems and methods for treating a defective heart valve, for example the mitral valve. Referring to FIG. 1A, the anatomy of a heart 10 includes a left atrium (LA) 12 and a left ventricle (LV) 14. An aorta 16 receives blood from the left ventricle 14 through an aortic valve 18, which serves to prevent regurgitation of blood back into the left ventricle 14. A mitral valve 20 is positioned between the left atrium 12 and the left ventricle 14, and allows one-way flow of blood from the left atrium 12 to the left ventricle 14.

Figure 1B:
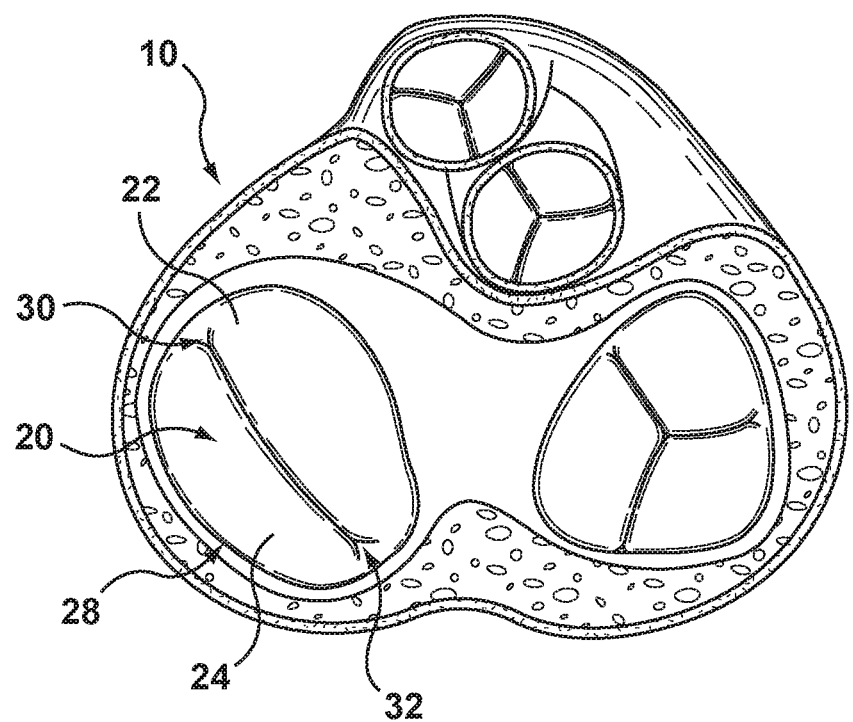
FIG. 1B is a simplified cross-sectional schematic view of the heart and illustrating some anatomical features of the mitral valve.
Figure 1C:
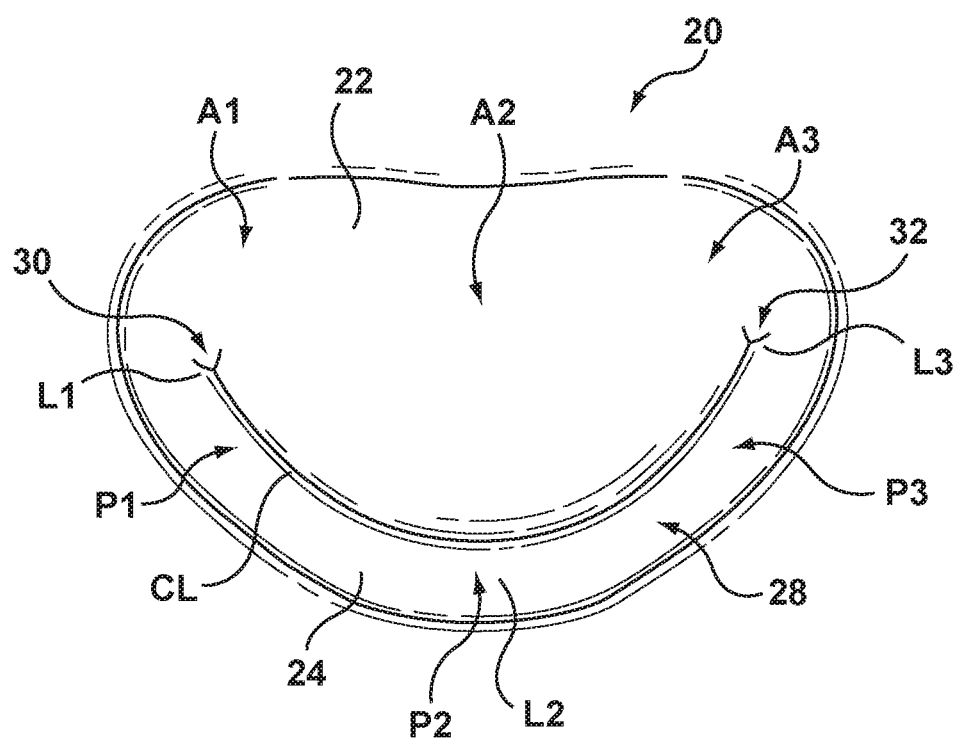
FIG. 1C illustrates additional anatomical features of the mitral valve.

The mitral valve 20 includes an anterior leaflet 22 and a posterior leaflet 24 that are coupled to chordae tendonae (not shown) that serve as "tension members" that prevent the leaflets 22, 24 of the mitral valve 20 from going past their closing point and prolapsing back into the left atrium. FIG. 1B illustrates the mitral valve 20 (in systole) from a different vantage point. A fibrous mitral valve annulus 28 provides attachment for the anterior and posterior leaflets 22, 24. The anterior and posterior leaflets 22, 24 are dissimilarly shaped. The anterior leaflet 22 is more firmly attached to the annulus 28, and is somewhat stiffer than the posterior leaflet 24 that is attached to the more mobile posterior lateral mitral annulus. The coaptation zone between the leaflets 22, 24 is not a simple line, but rather a curved, funnel-shaped surface interface. As best shown in FIG. 1C, commissures 30, 32 are where the anterior leaflet 22 meets the posterior leaflet 24. The coaptation zone is generally along a curved line CL. The leaflet 22, 24 edges are scalloped, more so for the posterior leaflet 24 then the anterior leaflet 22. Three scallop or segmented areas are generally defined along the anterior and the posterior aspects of the mitral valve annulus 28, and are commonly referred to as the A1, A2, and A3, and P1, P2, and P3 segments.

Figure 2A:
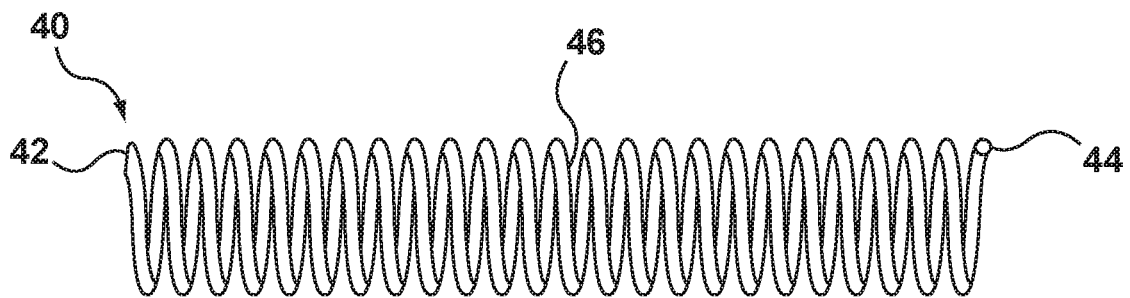
FIGS. 2A and 2B illustrate a helical anchor useful with some annuloplasty systems and methods in accordance with embodiments hereof.
Figure 2B:
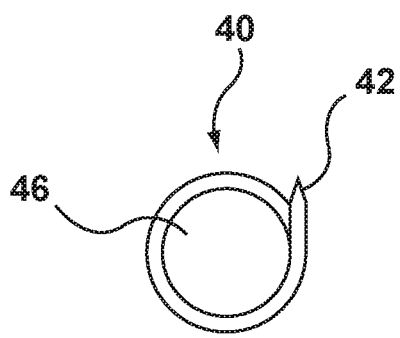

With the above general understanding of the mitral valve anatomy in mind, embodiments hereof relate to methods for delivering helical anchor coils to desired locations along the mitral valve annulus. The helical anchor coils can assume a wide variety of forms, and in some embodiments are similar to the helical anchor systems and devices disclosed in U.S. Publication No. 2007/0244553 ("the '553 publication") entitled "Annuloplasty Device Having a Helical Anchor and Methods for its Use", which is incorporated by reference herein in its entirety. For example, FIGS. 2A and 2B illustrate one embodiment of a helical anchor 40 useful with annuloplasty devices in accordance with embodiments hereof. The helical anchor 40 comprises an elongate coiled member having a tissue penetrating tip 42 at a distal end that is opposite a proximal end 44. The coils of the helical anchor 40 define a structure having a generally cylindrical shape, and the tip 42 extends on a tangent away from the circular perimeter of the helical anchor 40. Angling the sharpened tip 42 away from the exterior perimeter of the helical anchor 40 makes it easier for the tip 42 to penetrate a valve annulus when the helical anchor 40 is being rotated out of a delivery member and along an anchor guide. The helical anchor 40 can comprise a biocompatible metallic or polymeric material having suitable resiliency. The coils of the helical anchor 40 define an inner channel 46 for receiving a tether (not shown). As described in the '553 publication, the tether can be a flexible elongated filament of biocompatible material such as nylon or polyester.

Figure 3A:
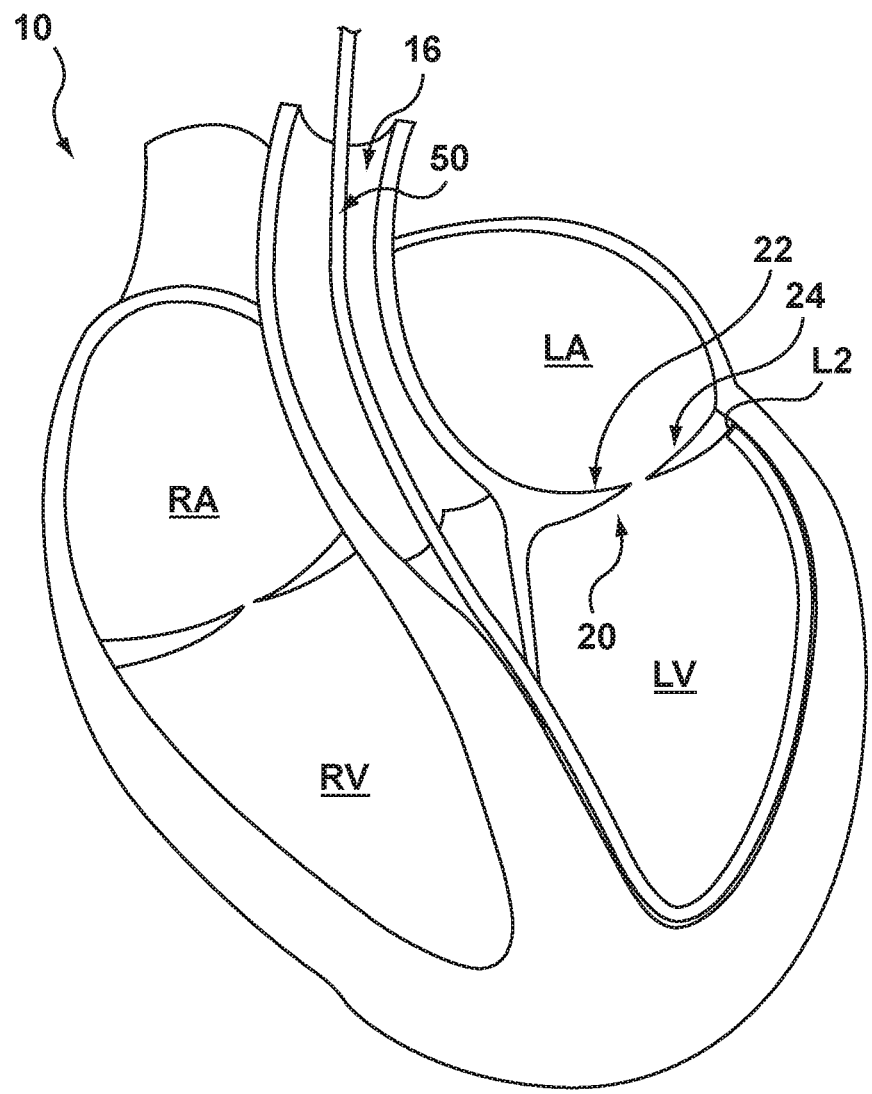
FIGS. 3A-3D illustrate a system and method for locating and identifying designated anatomical positions along the mitral valve annulus in a minimally invasive procedure in accordance with an embodiment hereof.
Figure 3B:
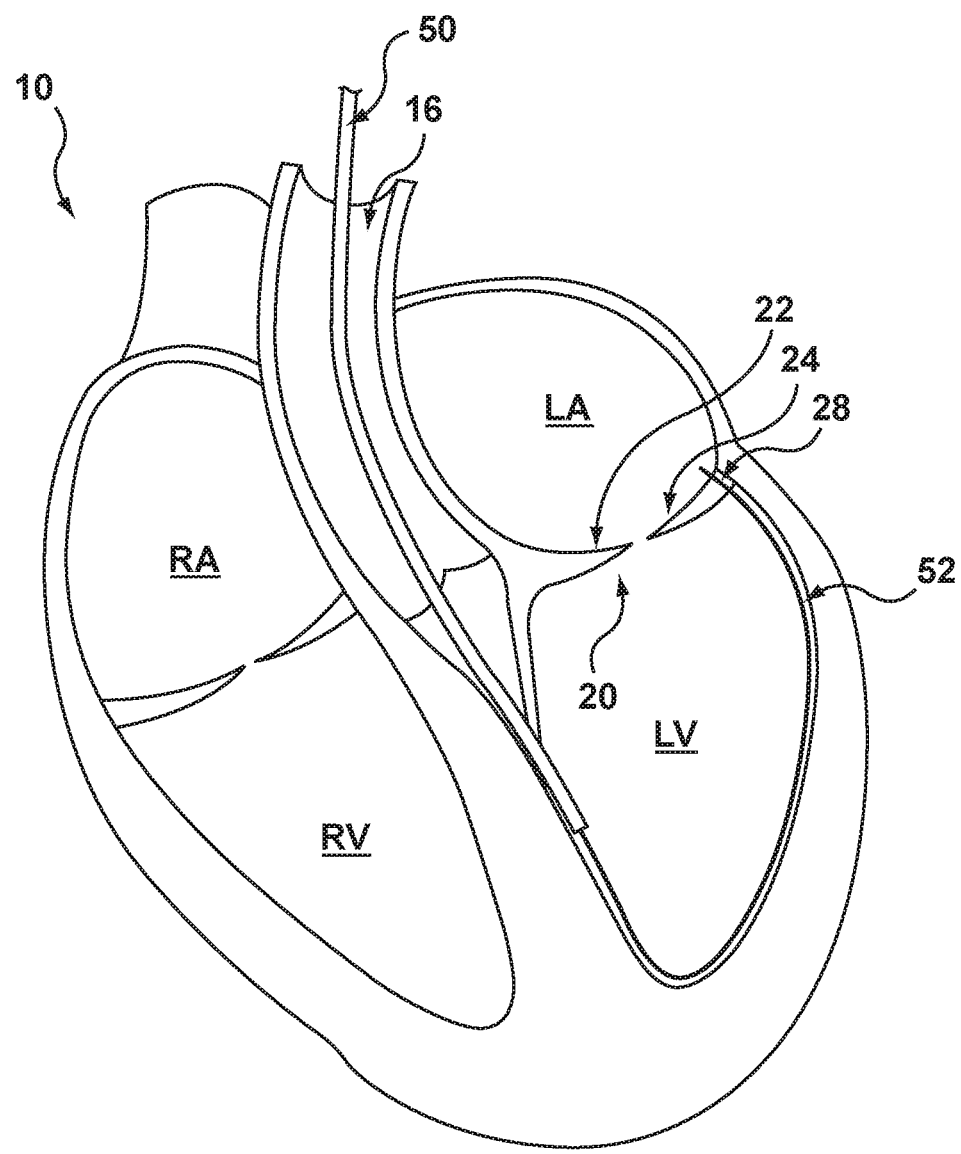
Figure 3C:
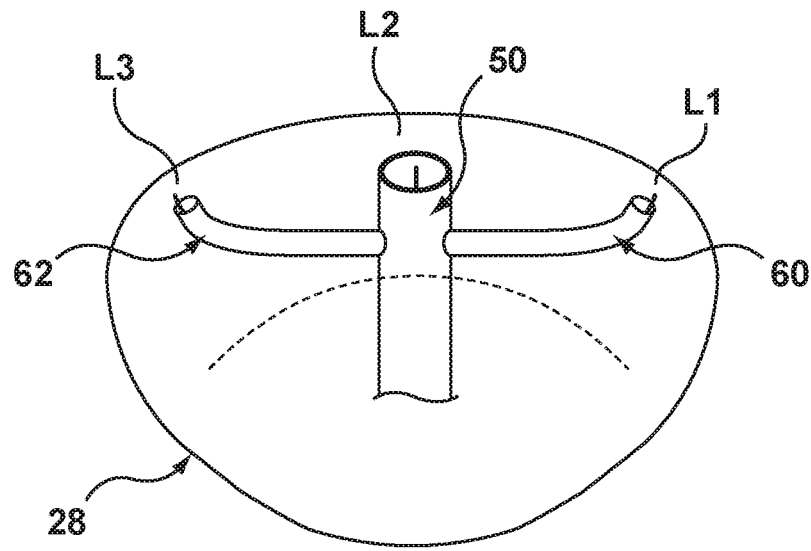
Figure 3D:
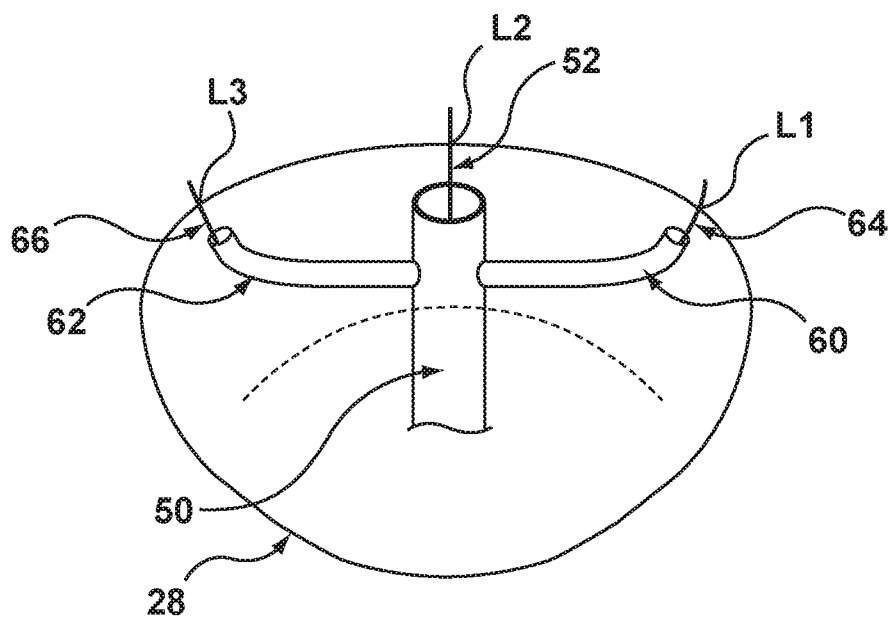

Returning to FIG. 1C, some systems and methods in accordance with embodiments hereof for delivering and implanting one or more of the helical anchors 40 include locating and marking the mitral valve annulus 28 at three locations or points L1-L3 via a percutaneous approach. The first and third locations L1, L3 correspond with the commissures 30, 32, whereas the second location L2 approximates a mid-point of the posterior leaflet 24 along the annulus 28 (i.e., mid-point of the middle posterior segment P2). A purpose of marking the three locations L1-L3 is to provide reference points for desired location of the subsequently implanted helical anchor(s) 40 (FIG. 2A). In one embodiment with reference to FIG. 3A, a primary catheter 50 is directed to and placed at the second location L2 from the ventricular side of the mitral valve 20. A guide wire (not shown) can be utilized to direct the primary catheter 50 to the second location L2. For example, FIG. 3B illustrates a primary guide wire 52 extending from the primary catheter 50 and piercing through the mitral valve annulus 28 at the second location L2. As a point of reference, it has been found that the mitral valve annulus 28 can be accessed from the ventricular side; directly underneath the annulus 28 is a sub-annular groove that the primary guide wire 52 conforms to throughout the region of the annulus 28 associated with the posterior leaflet 24. With the primary catheter 50 effectively anchored at the second location L2 via the primary guide wire 52, a sheath (not shown) of primary catheter 52 is retracted such that two secondary catheters 60, 62 laterally extend from a distal portion of the primary catheter 50 as shown in FIG. 3C. The secondary catheters 60, 62 are pre-shaped to correlate with the general curvature of the mitral valve annulus 28, and are thus precurved to terminate at the first and third locations L1, L3 when deployed to extend from the primary catheter 50 (with the primary catheter 50 located at L2). In embodiments in accordance herewith, secondary catheters 60, 62 may be portions of an integrated structure with primary catheter 50, or may be independent structures therefrom. As shown in FIG. 3D, secondary guide wires 64, 66 are then deployed through the secondary catheters 60, 62, respectively, and thus located at L1, L3. Locations L1-L3 are marked by the guide wires 64, 52, 66.

Figure 4A:
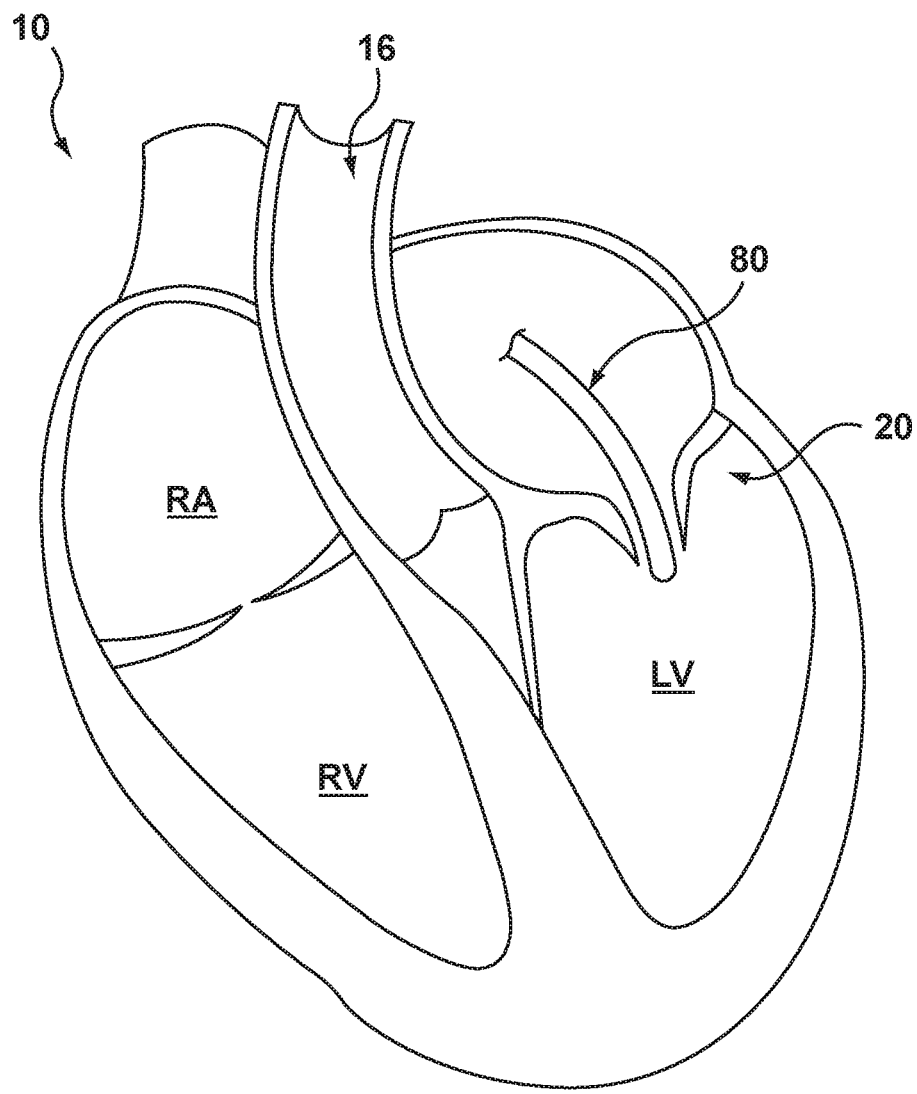
FIGS. 4A-4C illustrate another system and method for locating and identifying designated anatomical positions along the mitral valve annulus in a minimally invasive procedure in accordance with an embodiment hereof.
Figure 4B:
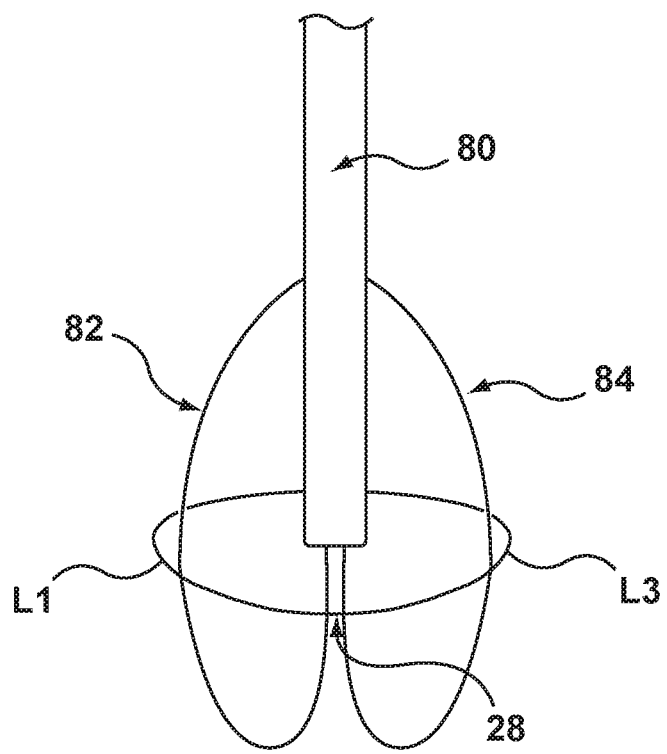
Figure 4C:
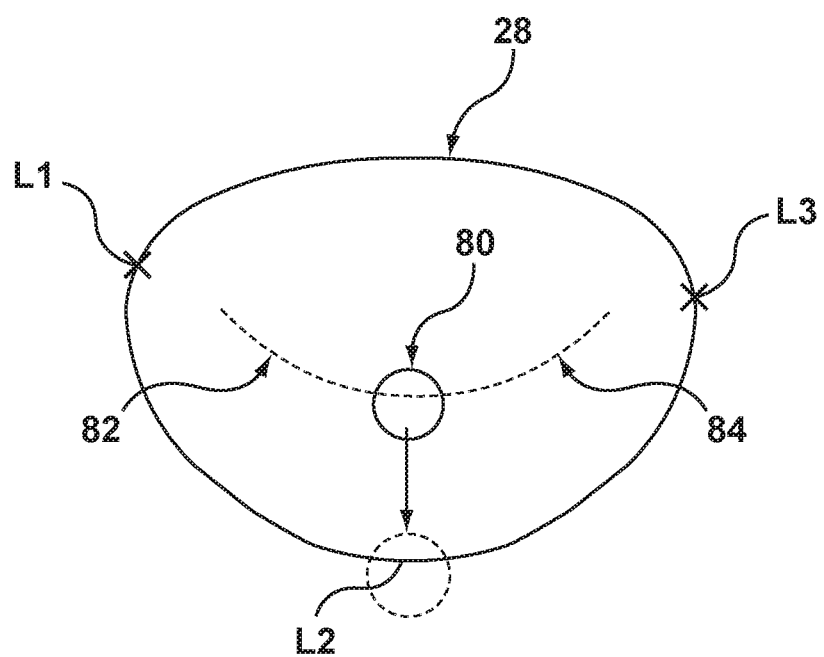
Figure 4D:
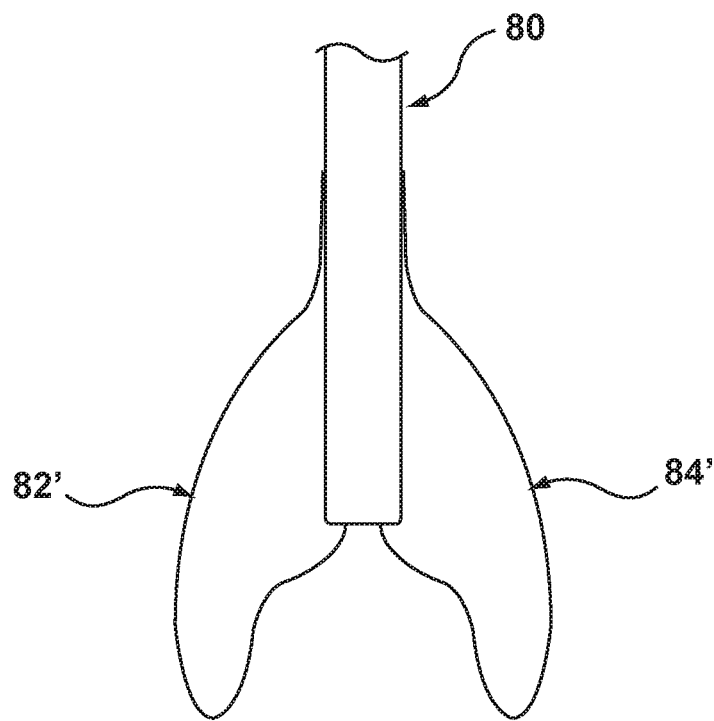
FIGS. 4D and 4E illustrate another system and method for locating and identifying designated anatomical positions along the mitral valve annulus similar to those of FIGS. 4A-4C.
Figure 4E:
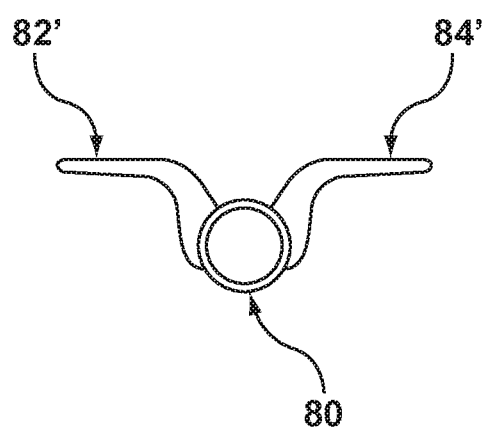

Another embodiment of a system and method for locating and marking the locations L1-L3 is generally reflected in FIGS. 4A-4C. A catheter 80 is placed through the mitral valve 20 via a trans-septal approach as shown in FIG. 4A. Once across the mitral valve 20, opposing, self-expanding loops 82, 84 are deployed from the catheter 80 as reflected by FIG. 4B, and act as a two-armed centering device. More particularly, upon being released from the catheter 80, the loops 82, 84 naturally expand to a set shape and self-locate the first and third locations (commissure points) at L1 and L3. The opposing loops 82, 84 are built at an angle slightly less than 180 degrees so that when opened further (relative to the catheter 80), the arms or loops 82, 84 are constrained against the mitral valve annulus 28 and thus "push" the catheter 80 towards the second location L2 as shown by dashed lines in FIG. 4C. As a result, the two arms 82, 84 are located at L1 and L3, and the catheter 80 is at L2 and are thus available for guided placement of one or more markers, anchors, etc. (not shown). In a related embodiment of FIGS. 4D and 4E, the self-expanding loops 82', 84' have a natural or predefined shape formed in accordance with an anatomy of the valve (e.g., mitral valve) such that when deployed from the catheter 80, the loops 82', 84' present minimal, if any, interference with functioning of the valve leaflets.

Figure 5A:
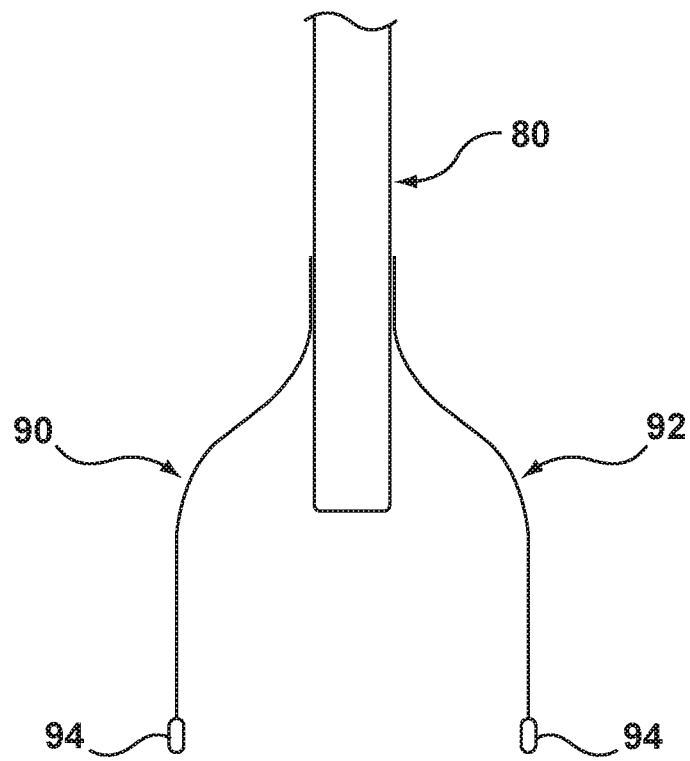
FIGS. 5A and 5B illustrate another system and method for locating and identifying designated anatomical positions along the mitral valve annulus in a minimally invasive procedure in accordance with an embodiment hereof.
Figure 5B:
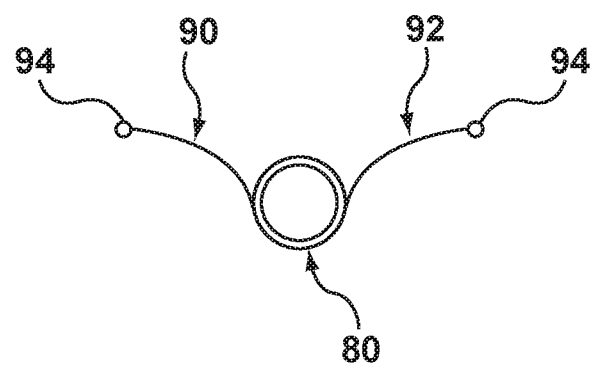

Another embodiment of a system and method for locating and marking the locations L1-L3 is generally reflected in FIGS. 5A and 5B, and is similar to those of FIGS. 4A-4E. Wires 90, 92 are employed in place of the loops 82, 84 (FIG. 4B) and can be flat wires. The wires 90, 92 are slightly stiffer then the loops 82, 84, and self-revert to the shape memory format shown in FIGS. 5A and 5B when deployed from the catheter 80. A distal tip 94 of each of the wires 90, 92 can be a ball or loop or other shape that renders the distal tip 94 less traumatic to contacted tissue. The system of FIGS. 5A and 5B can be employed to locate the locations L1-L3 in a manner similar to that described above with respect to FIGS. 4A-4C.

Figure 6:
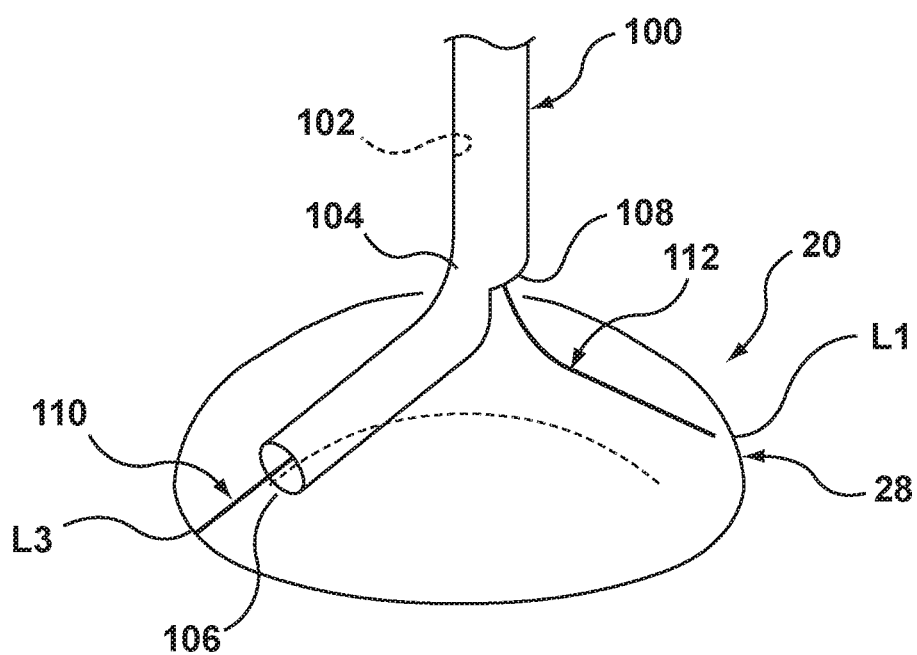
FIG. 6 illustrates another system and method for locating and identifying designated anatomical positions along the mitral valve annulus in a minimally invasive procedure in accordance with an embodiment hereof.

With reference to FIG. 6, another embodiment of a system and method for locating L1-L3 entails placing a catheter 100 above the mitral valve 20 via a trans-septal approach. The catheter 100 forms a lumen 102 along with a pre-formed bend 104 proximate a distal tip 106. An opening 108 to the lumen 102 is formed at the bend 104. First and second guide wires 110, 112 are slidably disposed within the lumen 102. With the catheter 100 located at the mitral valve 20, the first guide wire 110 is deployed through the distal tip 106 of the catheter 100 to locate L3 (or L1). The second guide wire 112 is deployed through the opening 108, and locates L1 (or L3). With the device of FIG. 6, L2 would not be marked. However, in a manner similar to that described above with respect to FIGS. 3A-3D, a piercing guide wire (not shown) could be placed retrograde through L2, and then guided out through the right side of the heart, and used to initially locate the tip of the device (not shown).

Figure 7A:
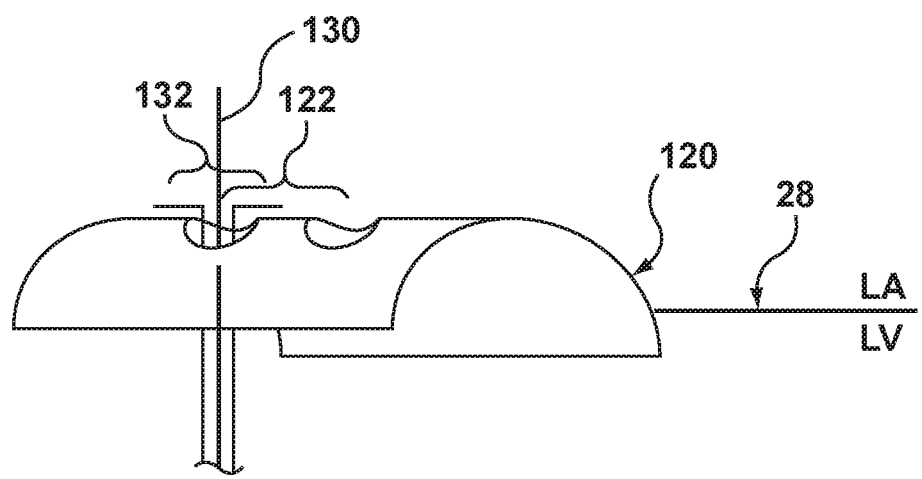
FIG. 7A-7C illustrate a guide useful in implanting the helical anchor of FIGS. 2A and 2B relative to the designated anatomical positions along the mitral valve annulus in accordance with an embodiment hereof.
Figure 7B:
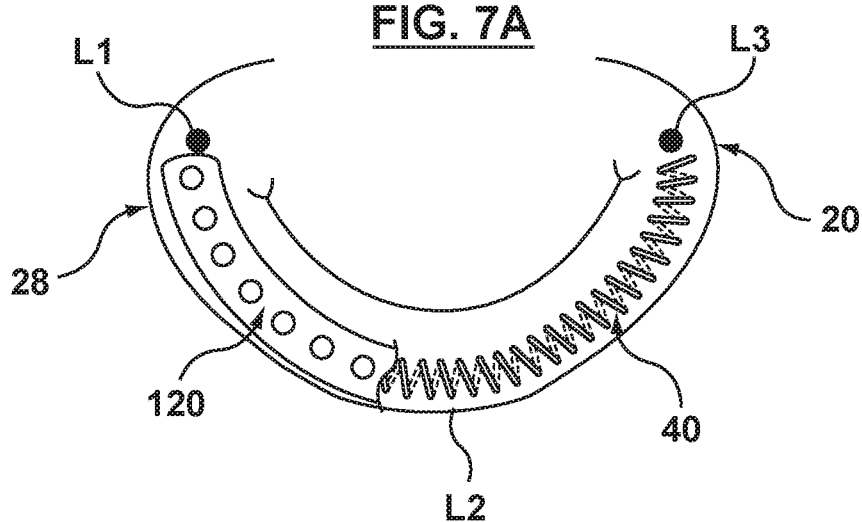
Figure 7C:
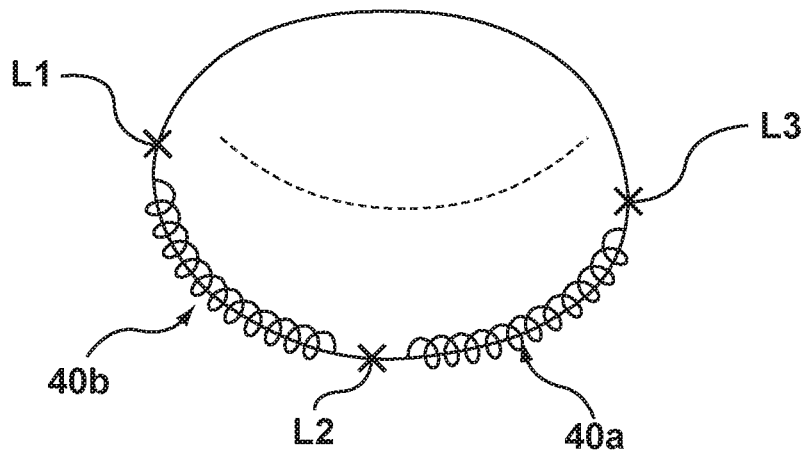

Using any of the embodiments described above, once guide wires have located the three key anatomical locations or positions L1, L2 and L3 around the posterior mitral valve annulus 28, a guide in accordance with an embodiment hereof is deployed for helical anchor 40 to follow. For example, FIG. 7A illustrates an embodiment of a guide 120. The guide 120 is a thin, elongated body in the form of a half circle. Within the half-circle are a series of circular guide holes 122 that extend perpendicular to an axis of the guide 120. In FIG. 7A, guide wire(s) 130 (one of which is shown in FIG. 7A) are shown having been previously placed in accordance with one of the methods as described above so as to puncture the annulus 28 from the ventricular side. The guide 120 is then placed on the atrial side of the annulus 28. The guide wire 130 is pushed through one of the guide holes 122. Clips 132 (or some other type of anchoring mechanism) are advanced through the guide holes 122 and pulled taut, maintaining the guide 120 in close proximity to the annulus 28. The half circle shape of guide 120 is then used to guide a helical anchor coil 40 from L1 to L3 (or from L3 to L1) as shown in FIG. 7B (as a point of reference, a portion of the guide 120 is cut away in FIG. 7B to better show the helical anchor coil 40 threaded into the annulus 28). Additionally, if guide wires had been used to locate each of L1-L3, then it is possible to deploy two shorter versions of the helical anchors 40. The first 40a would travel from L2 to L3, and the second 40b would travel from L2 to L1 as shown in FIG. 7C. Regardless, a tether (not shown) can then be used to cinch the annulus 28 as described in the '558 publication.

Figure 8:
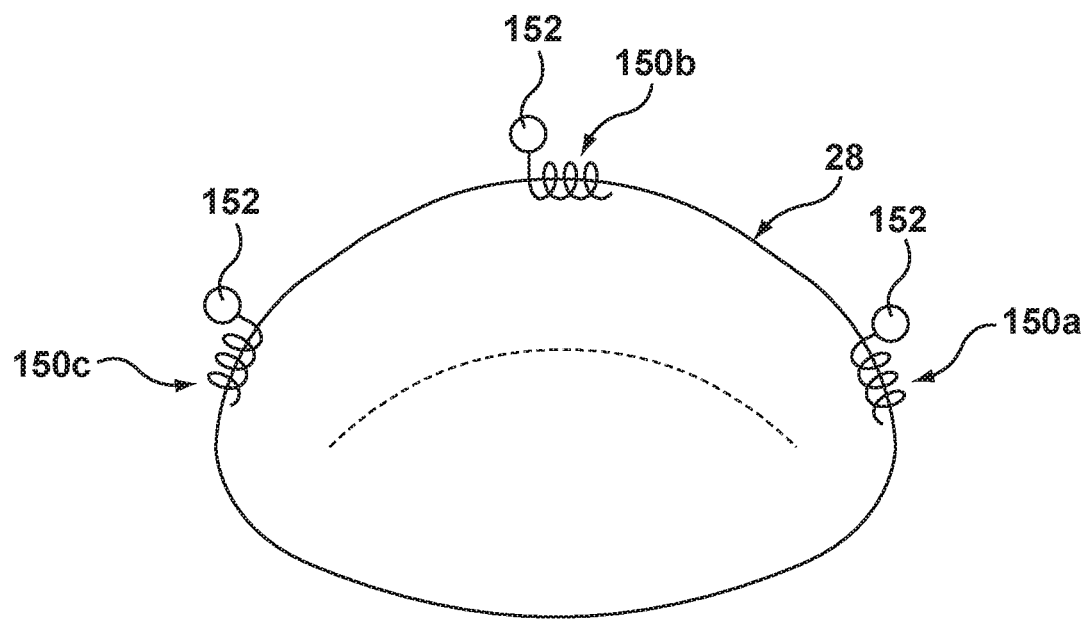
FIG. 8 is a schematic view of the mitral valve and illustrates helical anchors implanted to the mitral valve annulus and useful for modifying the annulus in accordance with some systems and methods in accordance with embodiments hereof.

In other embodiments hereof, with the locations L1-L3 located and identified as described in any of the above embodiments, instead of a helical anchor coil(s) 40 being threaded along through a perimeter of the annulus 28, short coil anchors 150a-150c can be turned through the tissue of the annulus 28 as shown in FIG. 8. The anchors 150a-150c are positioned so as to locate an eyelet 152 on the atrial side of the annulus 28. The helix of the anchors 150a-150c grasps the tissue, while the eyelets 152 can serve as an anchor to cinch against. The method for cinching can be a suture or some other material threaded through the eyelets 152 and pulled taut.

Figure 9:
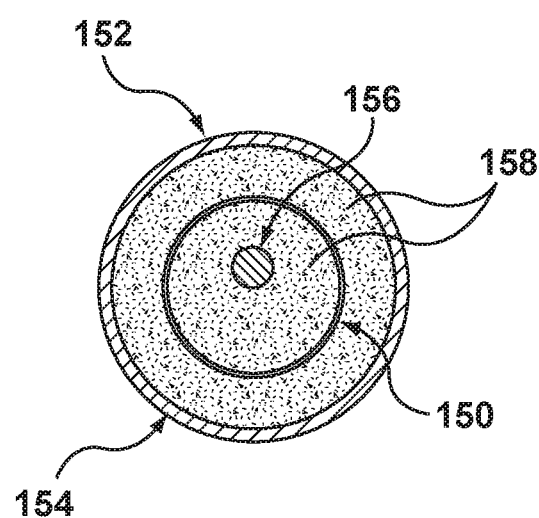
FIG. 9 is a simplified cross-sectional view of a catheter assembly useful for delivering the helical anchors of FIG. 8.

The coil anchors 150a-150c can individually be delivered to the annulus 28 via a catheter. For example, FIG. 9 schematically illustrates a catheter assembly 152 for delivering the coil anchor 150, and includes a catheter 154, a guide wire 156 and a foam 158. The coil anchor 150 is pre-shaped to keep from going straight. The pitch of the screw of the coil anchor 150 needs to be large enough to allow cinching, but small enough that it follows the curve and the guide wire 156. Depth of bite, the balance of size, engagement with the tissue, and clearance for cinching can be accounted for by the coil configuration. The biodegradable foam 158 is provided for the coil 150 to pass through and prevent binding. The biodegradable foam 158 keeps the coil 150 from tipping up at its ends.

Figure 10A:
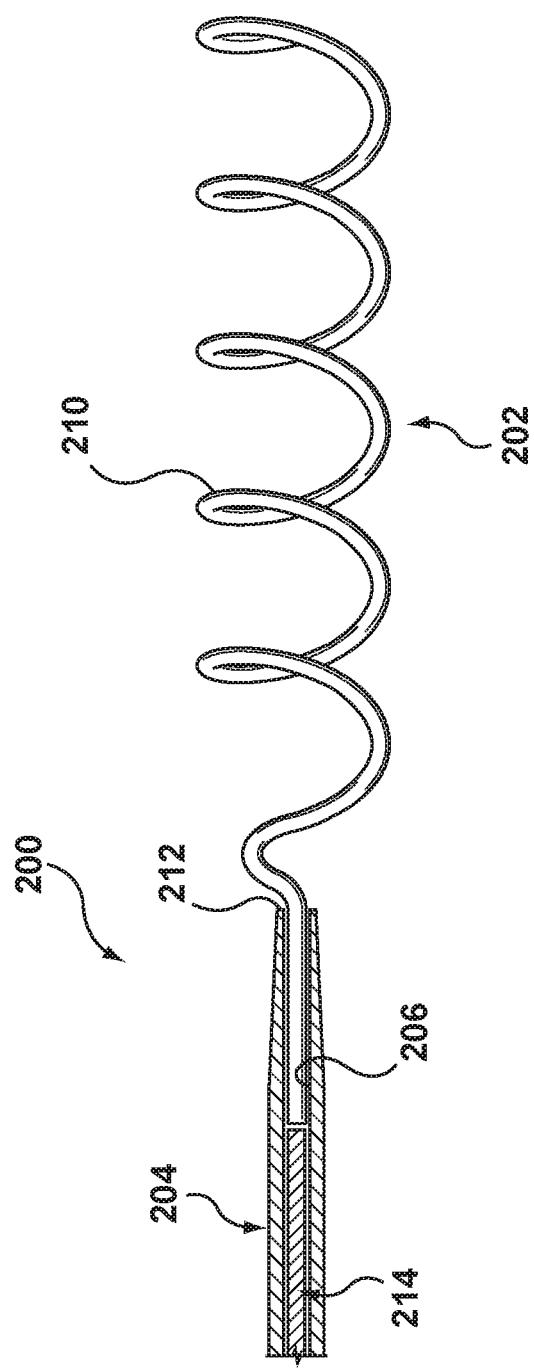
FIG. 10A is a simplified cross-sectional view of a needle system for modifying a heart valve annulus in a minimally invasive procedure and including a memory set helical anchor configured to self-revert from a substantially straight state to a coiled state.

While the above-described systems and methods of deploying helical anchor(s) envision delivering the helical anchor through a catheter to the delivery site in a coiled state, with securement of the helical anchor to the annulus tissue being accomplished by turning or rotating the helical coil, in other embodiments hereof, the helical anchor or coil can be delivered in a more straightened state. For example, FIG. 10A is a simplified view of an alternative system 200 in accordance with an embodiment hereof, and includes a helical anchor 202. The helical anchor 202 is delivered to an implantation site in a minimally invasive procedure via a needle 204. In this regard, FIG. 10A reflects that the helical anchor 202 naturally forms a coil, but can be rendered substantially straight when disposed within a lumen 206 of the needle 204. For example, the helical anchor 202 can be formed of a shape-memory material (e.g., nitinol) that is heat set to form a coil. As reflected by the distal section 210 identified in FIG. 10A, as the helical anchor 202 is released from a distal tip 212 of the needle 204, the helical anchor 202 self-reverts to the coil shape. FIG. 10B reflects that in other embodiments, the helical anchor 202' naturally forms a wavy line (as opposed to a true coil). Regardless, and returning to FIG. 10A, a push rod 214 is disposed within the lumen 206 of the needle 204 with a distal end of push rod 214 situated proximal to the helical anchor 202 to aid in deployment of the helical anchor from needle 204. Push rod 214 can be manipulated to distally advance the helical anchor 202 relative to the needle 204 and/or to keep the helical anchor 202 stationary as the needle 204 is retracted.

Figure 11A:
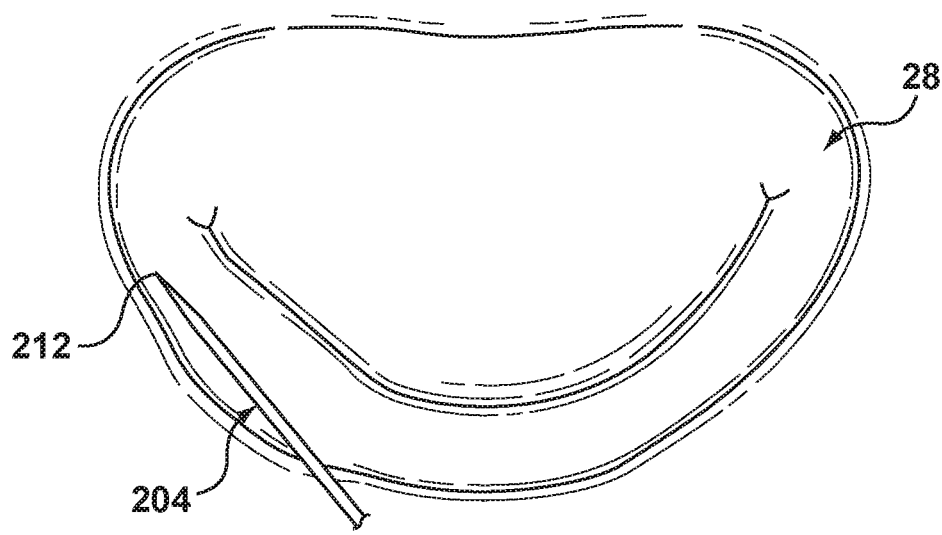
FIGS. 11A and 11B illustrate use of the system of FIG. 10A.
Figure 11B:
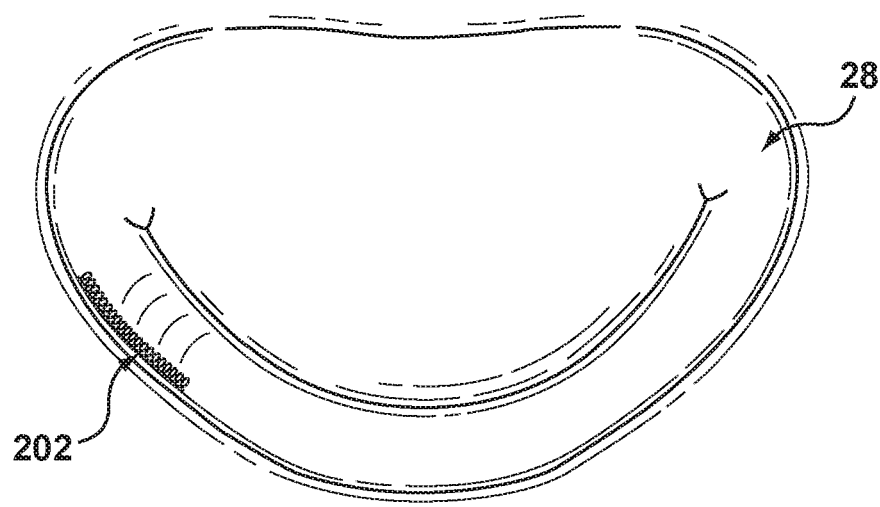

During use, the needle 204 is delivered to the valve annulus implantation site with the helical anchor 202 entirely disposed within the needle 204 (and thus constrained to a substantially straight shape). The distal tip 212 of needle 204 is initially inserted into the tissue of the annulus 28 as shown in FIG. 11A (it being understood that while the needle 204 is illustrated as being visible in FIG. 11A for ease of understanding, in actual practice the needle 204 will be disposed within a thickness of the annulus 28 tissue). FIG. 11A identifies one possible implantation site along the mitral valve annulus 28 in a relatively tangential direction. The needle 204 is then retracted proximally while the helical anchor 202 (FIG. 10A) held stationary (e.g., via the push rod 214 (FIG. 10A)). As the straightened helical anchor 202 is uncovered, it self-transitions from the constrained, substantially straight shape into the set coiled shape within the annulus tissue. During this transformation of the helical anchor 202, the annulus tissue is cinched as generally reflected in FIG. 11B (it being understood that while the helical anchor 202 is illustrated as being visible in FIG. 11B for ease of understanding, in actual practice the helical anchor 202 will be entirely disposed within a thickness of the annulus 28 tissue). The tissue is drawn together by the implanted helical anchor 202.

In some embodiments, when constrained by the needle 204 (FIG. 10A), the helical anchor 202 in its austenite form pushes against the walls of the needle 204, creating friction. As such, in some embodiments, the helical anchor 202 is selected to be relatively short (e.g., on the order of 1 inch in the straightened state), so that the frictional force can be overcome without binding. Further, the helical anchor 202 can be subjected to cooling while it is constrained within the needle 204 to keep the helical anchor 202 in its malleable martensite form, reducing the friction required. In yet other embodiments, coatings on the inside of the needle 204, such as a Teflon® coating may be useful in reducing the frictional force. Where desired, two or more of the relatively short helical anchors 202 can be implanted.

With the systems and methods of FIG. 10A, septal-lateral cinching is an effective means of reducing mitral regurgitation. In an animal model of functional mitral regurgitation (FMR), a reduction in mitral regurgitation severity from grade 2 to grade 0 was observed with a decrease in the septal-lateral diameter of the mitral annulus of 6.0±2.6 mm. Initial testing of prototype devices measured the change in tissue length when deployed on a cadaveric swine heart to be 6.35 mm.

Figure 12A:
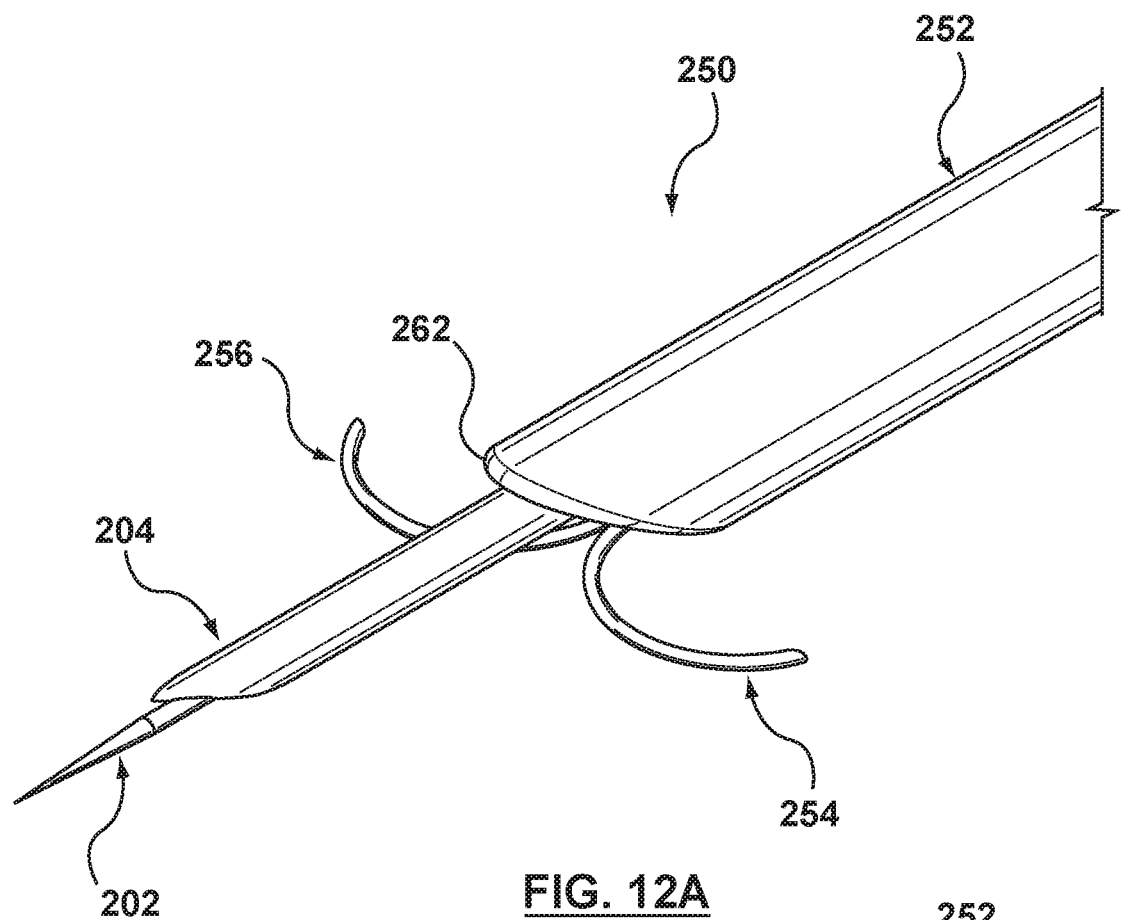
FIGS. 12A and 12B illustrate a delivery system useful with the needle system of FIG. 10A.
Figure 12B:
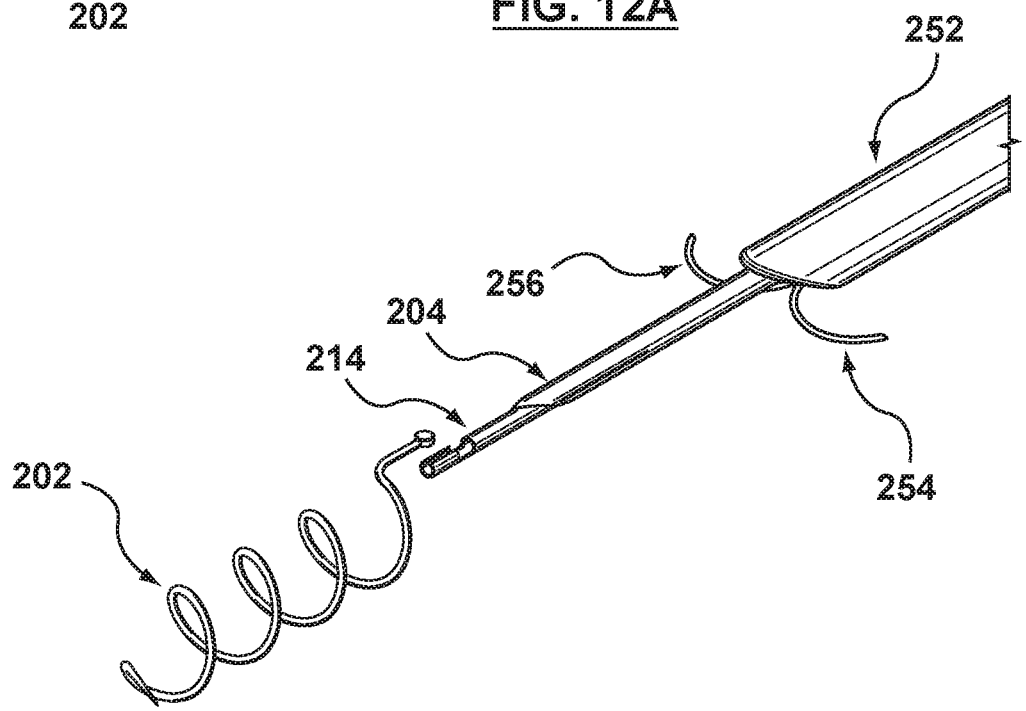

A related embodiment delivery system 250 for delivering and implanting the helical anchor 202 is shown in FIG. 12A, and includes a delivery catheter 252 and opposing clips 254, 256. In an embodiment, the pair of clips 254, 256 has opposing curved ends when deployed from a distal end 262 of the catheter 252. The catheter 252 forms a first lumen 258 sized to slidably receive the needle 204 (that otherwise slidaby retains the helical anchor 202 as described above). The opposing clips 254, 256 are retained or disposed within a second lumen 260 of the catheter 252, with the second lumen 260 being sized to permit clips 254, 256 to be slidably deployed therefrom. The lumens 258, 260 are open to a distal tip 262 of the catheter 252. Distal tip 262 of catheter 252 may also be referenced to herein as the distal end of catheter 252. The clips 254, 256 serve as a mechanism for initially attaching the delivery system 250 to the valve annulus. This will allow the user to accurately and reliably insert the needle 204 by serving as an anchor. Additionally, the clips 254, 256 allow the user to push on the needle 204 and gently pull on the clips 254, 256 during needle insertion, increasing the ability to puncture the tissue with the needle 204. FIG. 12B illustrates the assembly 250 in a deployed state in which a distal portion of the needle 204 is distally extended beyond the catheter 252 but retracted relative to a distal end of push rod 214, such that the helical anchor 202 is deployed from the lumen of needle 204 and returned to its coiled state.

Figure 13A:
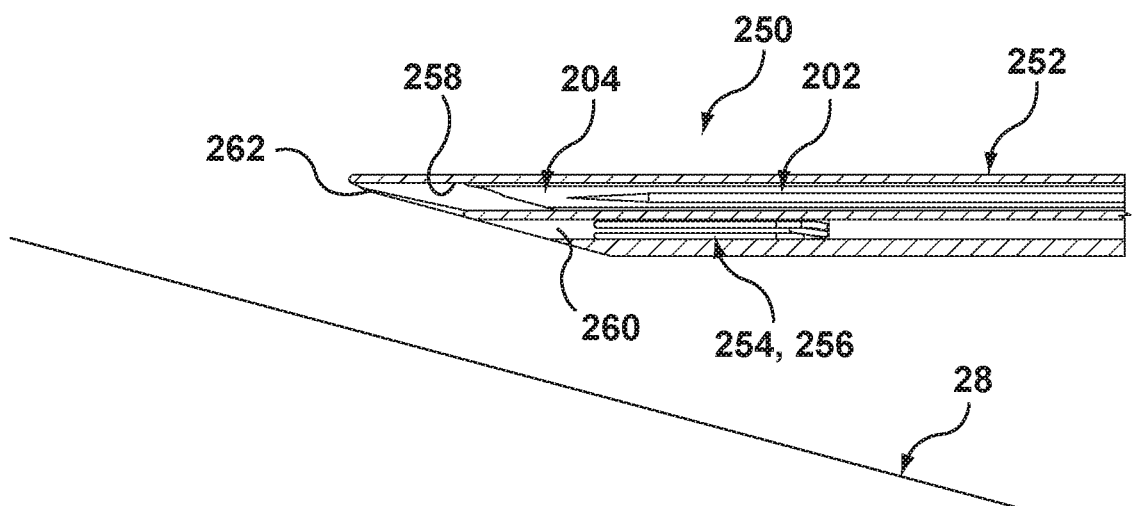
FIGS. 13A-13I illustrate use of the delivery system of FIGS. 12A and 12B.
Figure 13B:
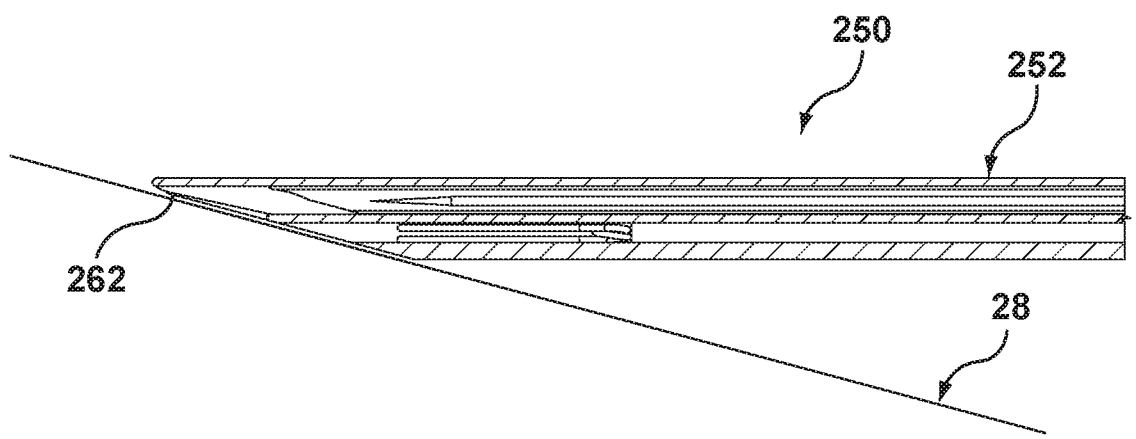
Figure 13C:
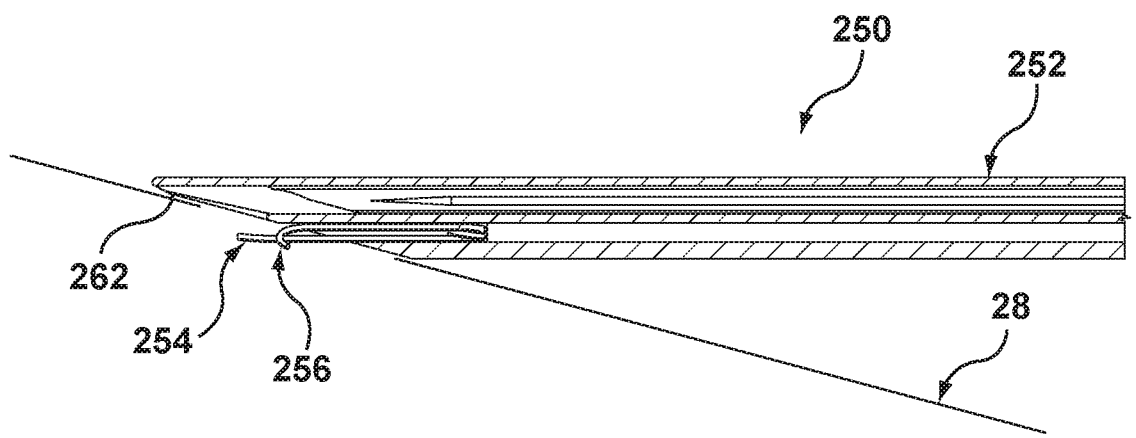
Figure 13D:
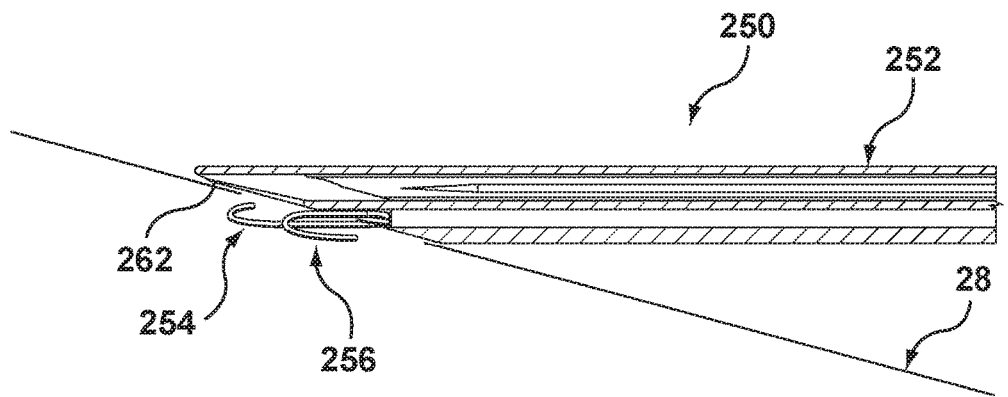

A method of using the system 250 in implanting the helical anchor 202 is shown in FIGS. 13A-13I. With reference to FIG. 13A, the needle 204 is sheathed within the catheter 252, and the helical anchor 202 is loaded within the needle 204. The catheter 252 is directed to the mitral annulus, for example through a steerable overtube or sheath (not shown) via a trans-septal puncture or a left atrial approach. FIG. 13A further reflects that the distal tip 262 of catheter 252 can have a tapered shape, or stated another way can form an angled surface with respect to a longitudinal axis of the catheter, such that a first opening or exit of the first lumen 258 within distal tip 262 extends distally beyond a second opening or exit of the second lumen 260 within distal tip 262. As shown in FIG. 13B, the catheter 252 is advanced from the sheath, bringing the tip 262 into contact with the mitral annulus 28 at the desired implant location. The clips 254, 256 are then deployed from the catheter 252 as shown in FIG. 13C. The deployed clips 254, 256 maintain the position of the catheter 252 relative to the annulus tissue 28. As shown in FIG. 13D, any rotational changes can still be made to ensure proper alignment with the annulus 28 and/or the septal-lateral diameter of the mitral valve 20 (FIG. 1A).

Figure 13E:
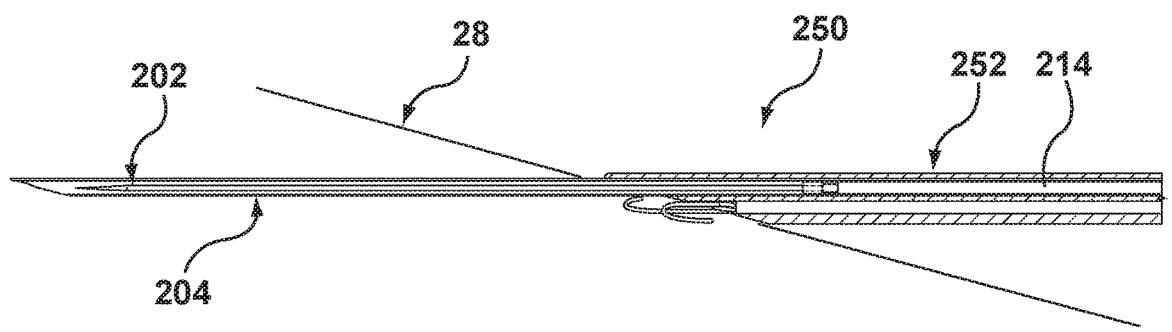

At FIG. 13E, the needle 204 (preloaded with the helical anchor 202 as described above) is advanced through the catheter 252 and into the annulus 28 tissue. In some embodiments, the needle 204 is advanced at an angle more parallel with the tissue surface than is otherwise reflected in the drawing. In some embodiments, the needle 204 can have a preformed bend (not shown) that will extend a set distance into and then run parallel with the tissue surface.

Figure 13F:
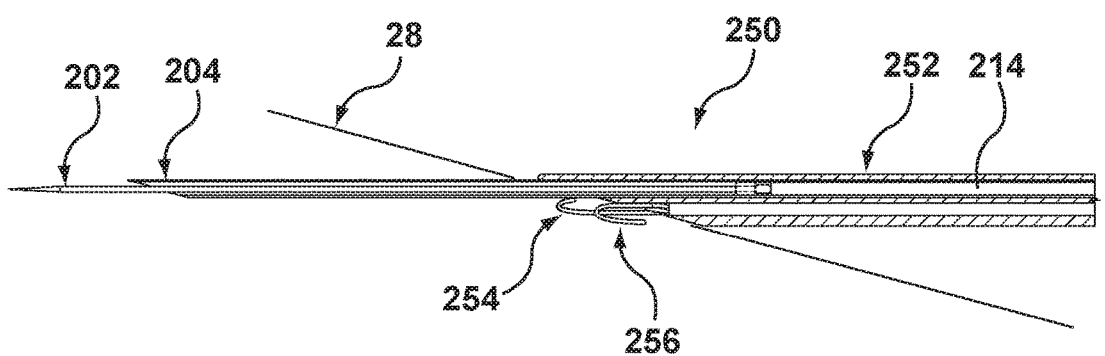
Figure 13G:
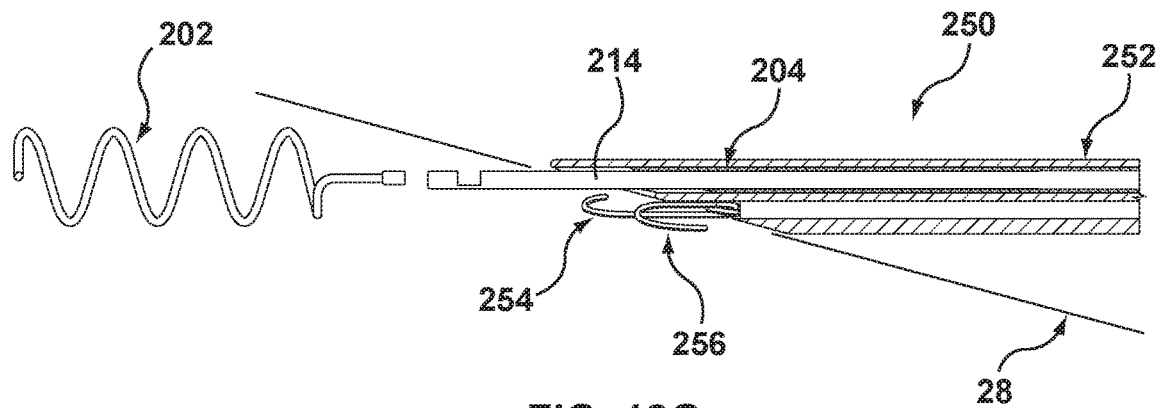
Figure 13H:
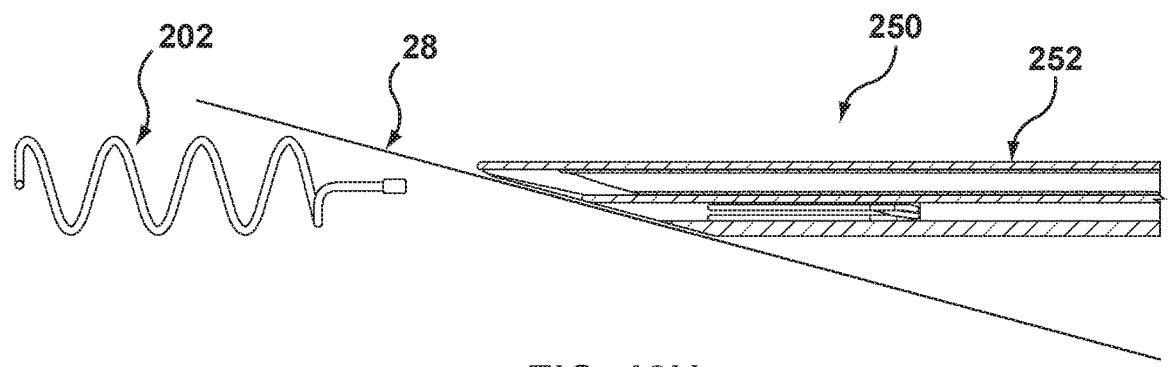
Figure 13I:
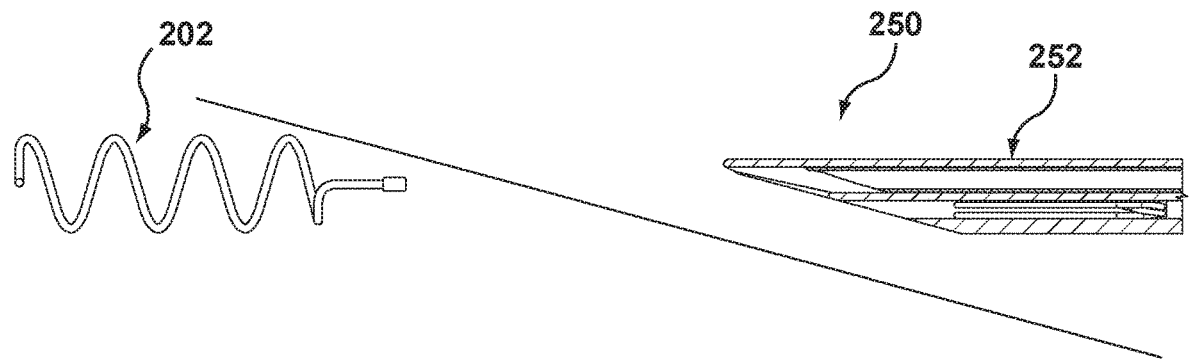

In FIG. 13F, the needle 204 is partially withdrawn from over the helical anchor 202 while push rod 214 is held stationary relative to catheter 252. FIG. 13G reflects that after the needle 204 is withdrawn into the catheter 252 and with push rod 214 distally extend therefrom, the helical anchor 202 is released and self-reverts to its preformed coil shape, cinching the engaged tissue. In FIG. 13H, the clips 254, 256 and push rod 214 are withdrawn back into the catheter 252, allowing the catheter 252 to be withdrawn from the implantation site as shown in FIG. 13I. The catheter 252 can be removed from the sheath, or the sheath can be steered to a new location and the process repeated for any additional helical anchor placements desired.

Figure 14:
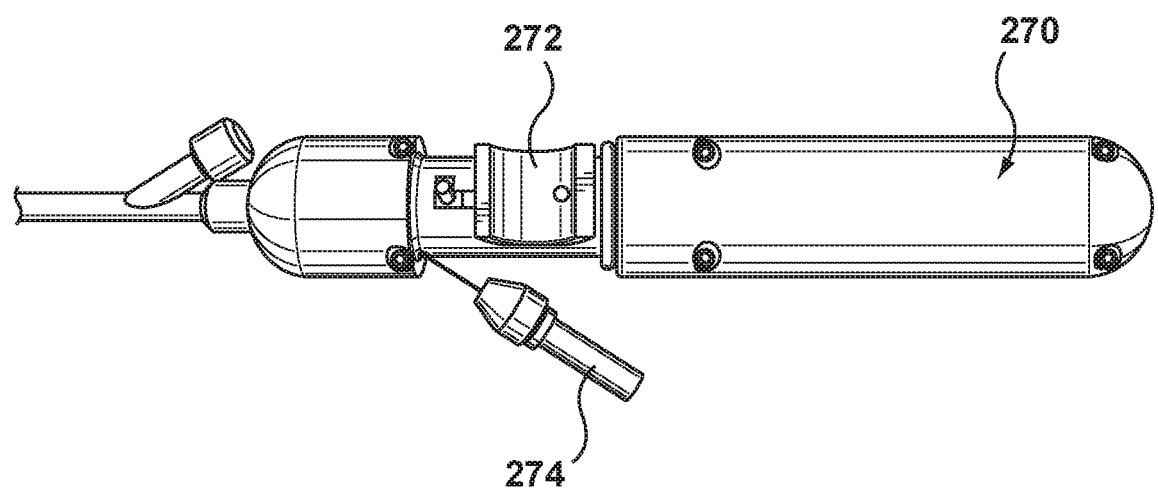
FIG. 14 illustrates a handle assembly useful with the delivery system of FIGS. 12A and 12B.

System 250 can include various actuators to effectuate desired manipulation of the clips 254, 256. For example, FIG. 14 illustrates a handle 270 in accordance with an embodiment hereof that may be used with the system 250. The handle 270 includes a needle deployment actuator 272 and a clip actuator 274.

Figure 15A:
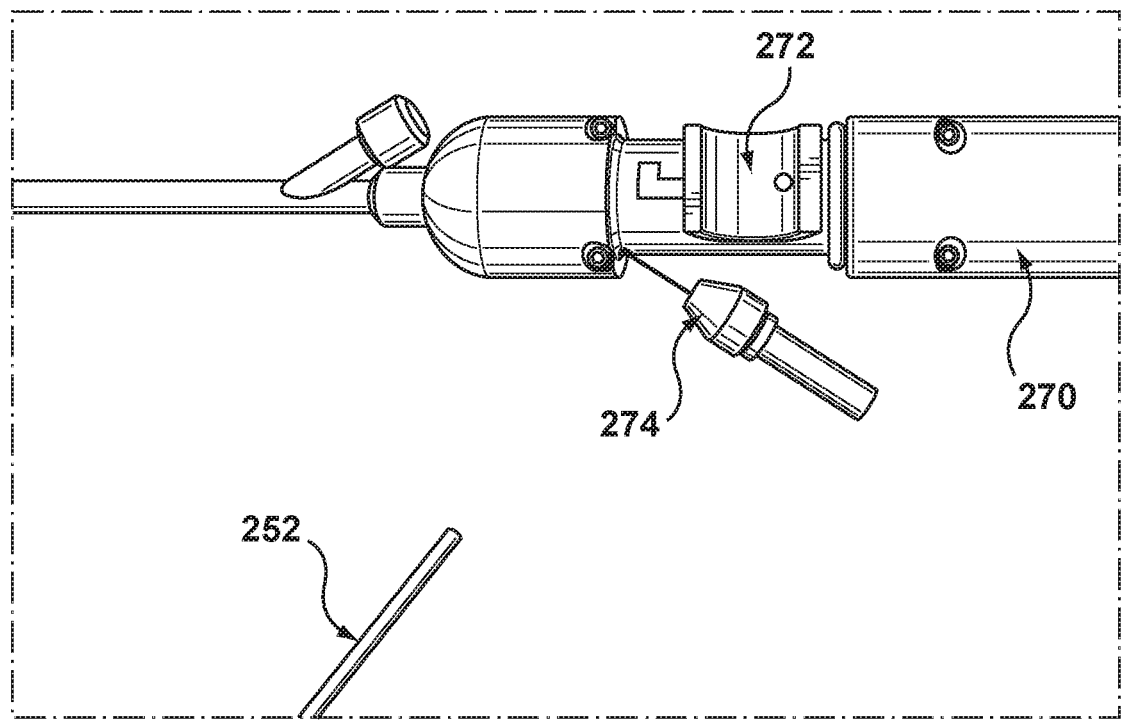
FIGS. 15A-15F illustrate use of delivery system of FIGS. 12A and 12B, and the handle assembly of FIG. 14.
Figure 15B:
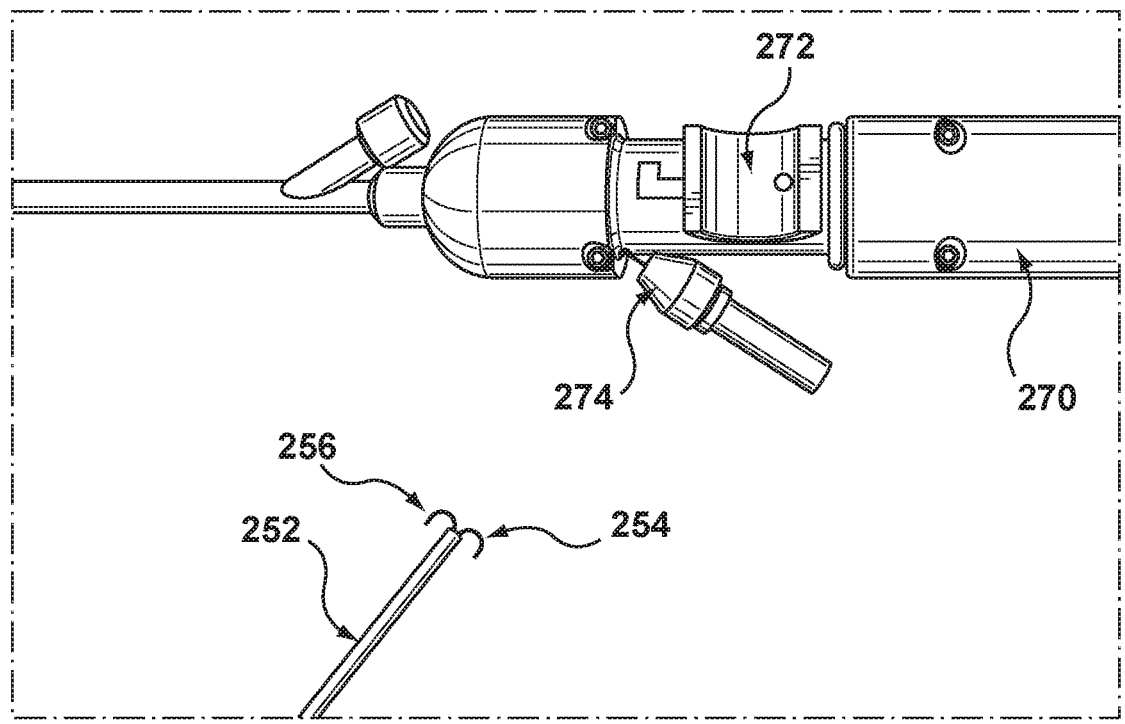
Figure 15C:
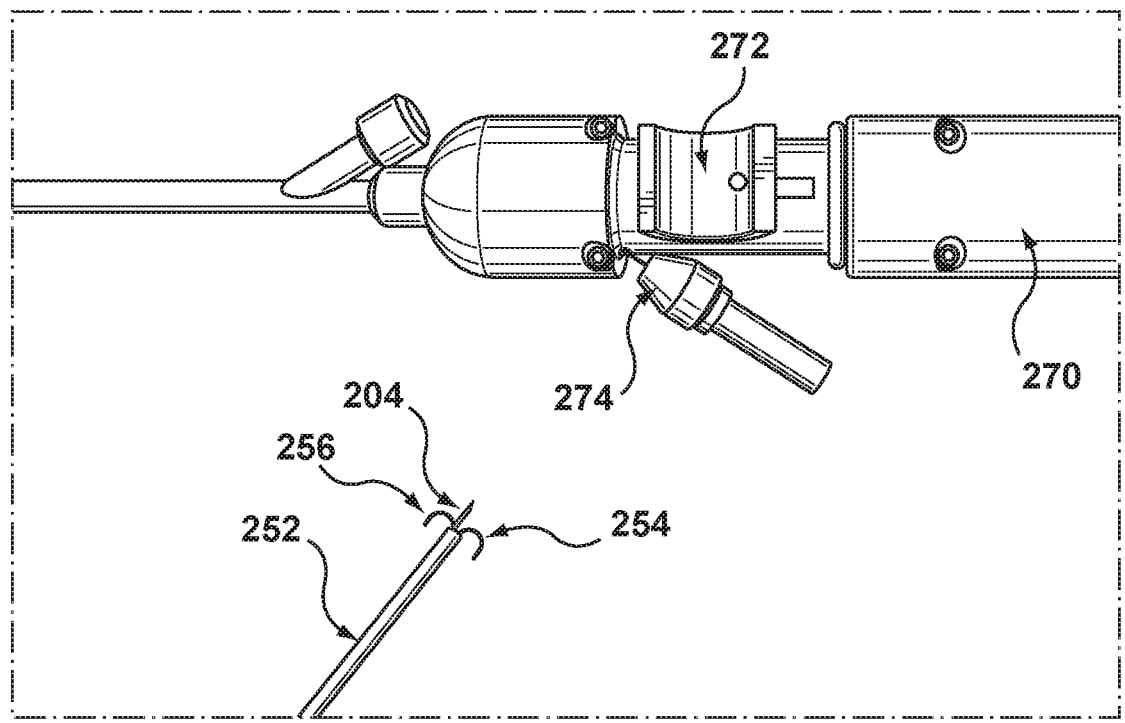
Figure 15D:
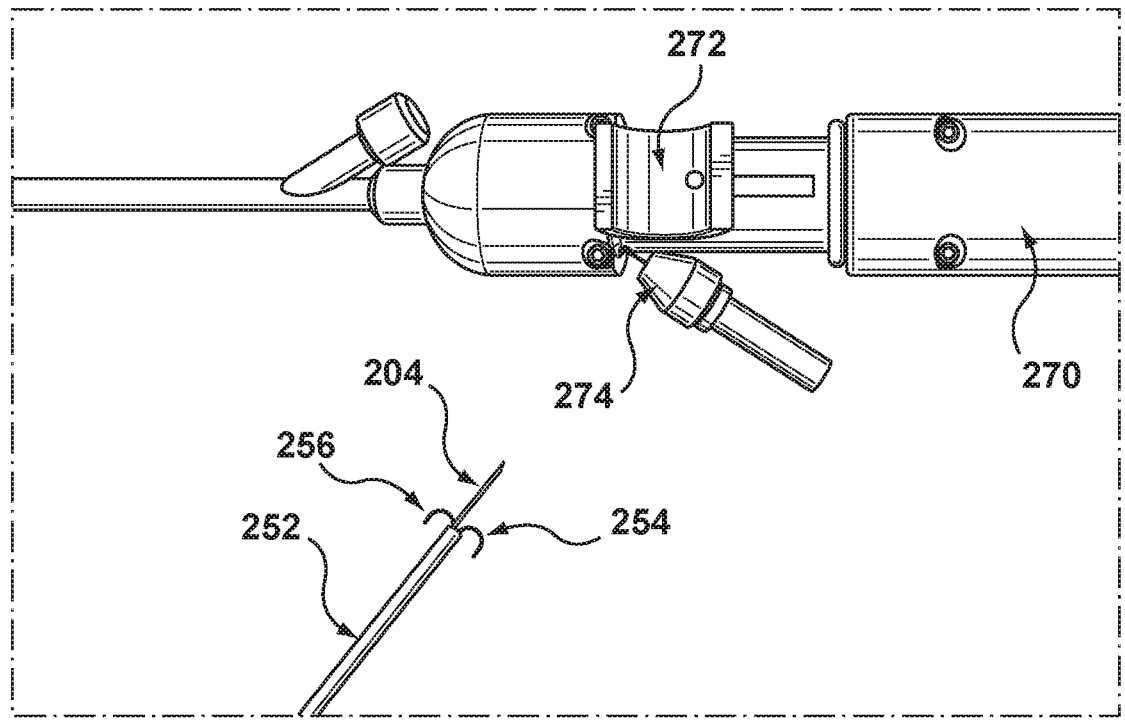
Figure 15E:
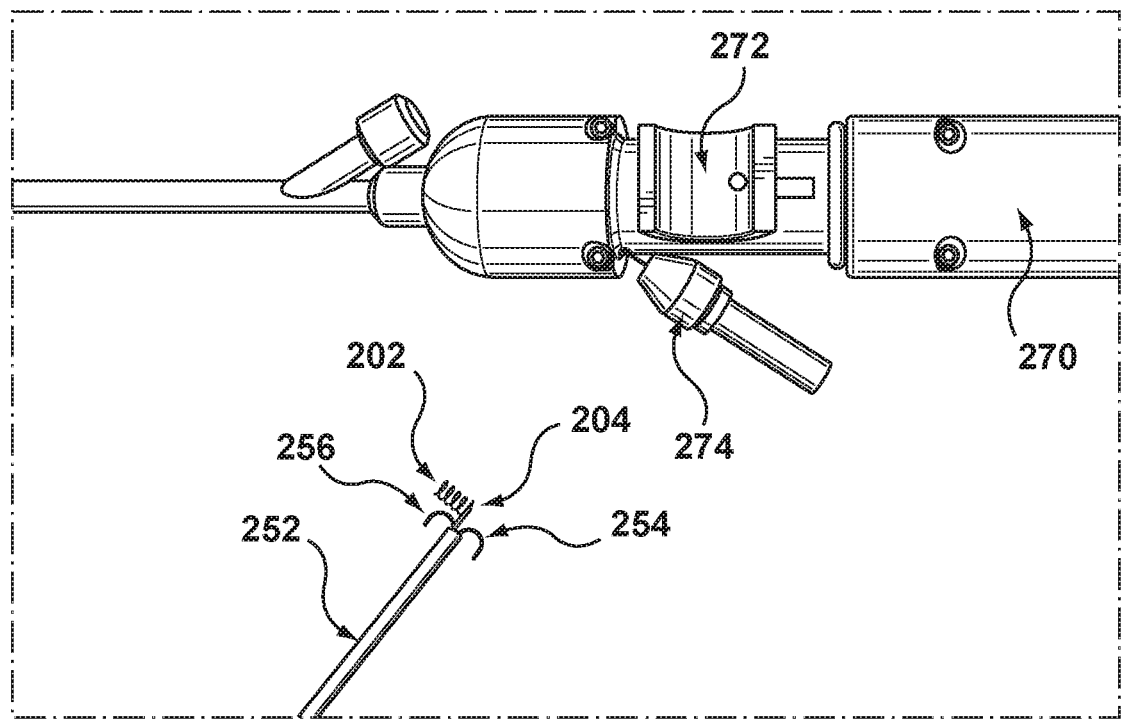
Figure 15F:
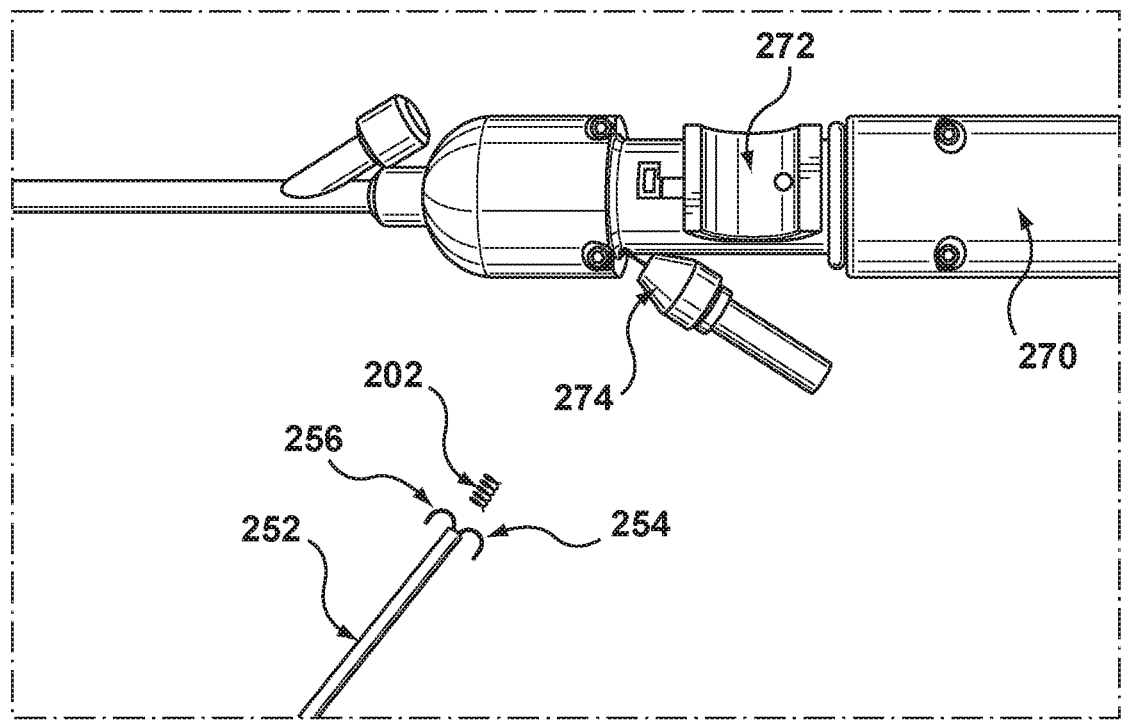

FIGS. 15A-15F depicts use of handle 270 in effectuating various deployment states at the distal tip 262 of catheter 252. For example, in FIG. 15A, the needle deployment actuator 272 and the clip actuator 274 are in a "home" position, with the clips (not shown) and the needle (not shown) retracted inside of the catheter 252. In FIG. 15B, the clip actuator 274 is actuated to advance or deploy the clips 254, 256. In FIG. 15C, the needle deployment actuator 272 is actuated to partially advance the needle 204. FIG. 15D reflects further advancement of the needle 204 prior to deployment of the helical anchor (not shown). In FIG. 15E, the mechanism for maintaining the helical anchor stationary relative to the needle 204 (e.g., the push rod 214 (FIG. 10A)) is locked. With retraction of the needle 204, then, the helical anchor 202 is deployed. Finally, FIG. 15F reflects the needle deployment actuator 272 returned to its original position, causing the helical anchor 202 to be fully deployed while the needle 204 (FIG. 15E) is captured inside of the catheter 252.

In some embodiments, the implanted helical anchor 202 effectuates cinching of the mitral valve annulus tissue. In related embodiments, RF energy can be applied to so-implanted helical anchor 202. The heat generated by the energized helical anchor 202 will cause collagen in the tissue to reorganize (i.e., shape change), and the mitral valve 28 will conform to the shape created by the coil. This change in the collagen structure will keep the desired repaired shape. In some embodiments, the helical anchor 202 may subsequently be removed from the annulus tissue, or alternatively can be left in place. The collagen remodeling may relieve possible stress on the helical anchor 202 from the annulus tissue that might otherwise influence the ability of the helical coil 202 to retract back to its preformed state.

Figure 16A:
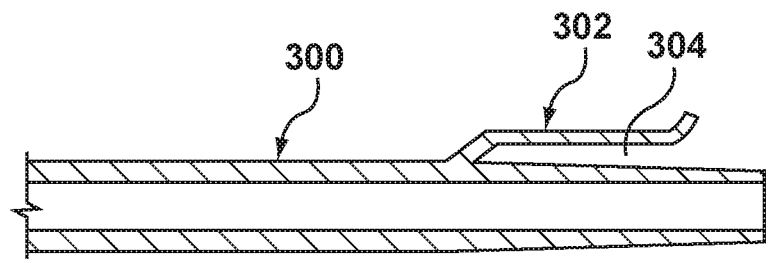
FIGS. 16A and 16B illustrate a needle system in accordance with another embodiment hereof.
Figure 16B:
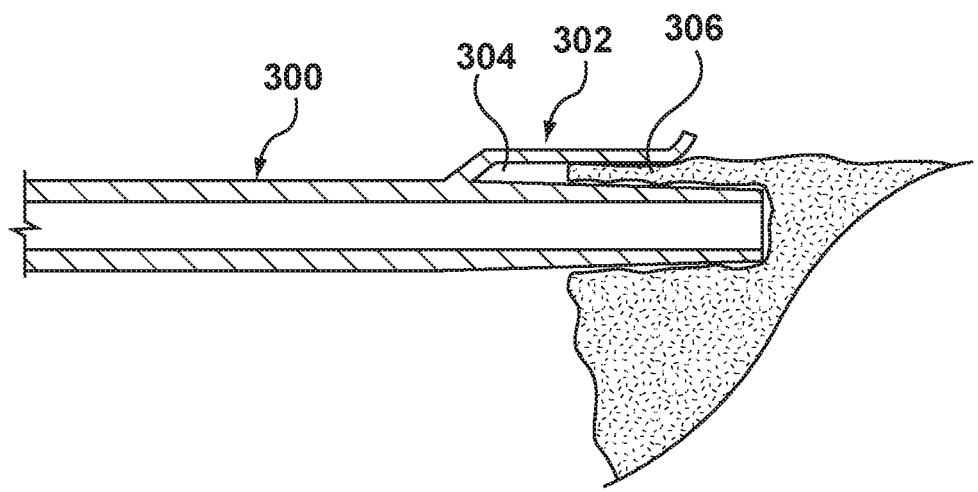

Another embodiment of a system for delivering the helical anchor 202 via the needle 204 is shown in FIG. 16A. In particular, FIG. 16A illustrates a needle 300 similar to the needle 204 described above, but further including a tracking arm 302. The tracking arm 302 projects from a distal portion of the needle 300, defining a channel 304 between an outer surface of the needle 300 and the tracking arm 302. As the distal portion of the needle 300 is introduced into the annulus, the tracking arm 302 is kept on the outside of the annulus, with a tissue layer 306 being captured within the channel 304 as shown in FIG. 16B. In this arrangement, the tracking arm 302 assists in tracking the needle 300 through the tissue, with the proximal juncture or end where the tracking arm 302 meets or is attached to the needle 300 acting as a stop to prevent the needle 300 from going too deep into the tissue or popping out of the annulus.

Figure 17:
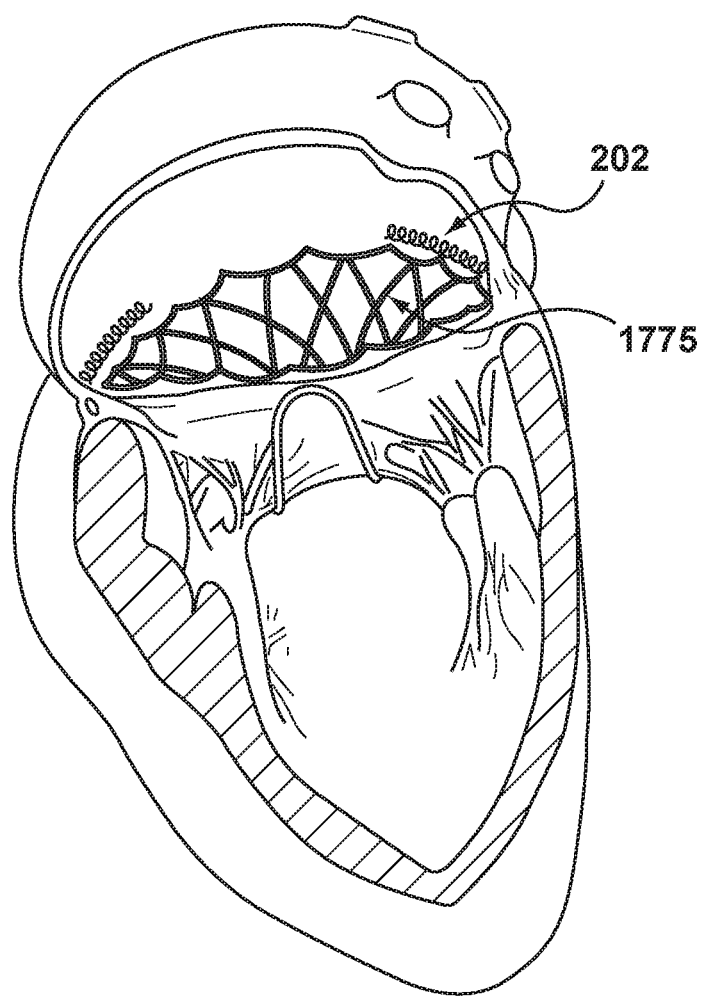
FIG. 17 illustrates a prosthetic cardiac valve implanted within a modified valve annulus in accordance with another embodiment hereof.

In other embodiments in accordance herewith, a method for delivering a helical anchor coil to a desired location along a valve annulus as described above is followed by implantation of a prosthetic cardiac valve within the modified valve annulus. In an embodiment as shown in FIG. 17, the structure of a native mitral valve annulus may be modified using one or more helical anchor coils 202 as described herein prior to the delivery and implantation of a prosthetic mitral valve 1775. Examples of percutaneously delivered prosthetic cardiac valves that may be implanted within a modified valve annulus as described herein are described, for example, in US Publication Nos. 2006/0265056, 2008/0140189, 2008/0071361, 2011/0208297, and 2012/0035722, each of which is incorporated by reference herein in its entirety. One or more helical anchor coils may be used to modify the shape of a valve annulus into a desirable shape or configuration for implantation of a prosthetic cardiac valve within the modified valve annulus. For example, a mitral valve annulus may be modified or shaped into a more rounded configuration that than provides a better fit for a transcatheter three leaflet prosthetic valve having a more rounded circumference or configuration.

While various embodiments have been described above, it should be understood that they have been presented only as illustrations and examples of the present invention, and not by way of limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the appended claims and their equivalents. It will also be understood that each feature of each embodiment discussed herein, and of each reference cited herein, can be used in combination with the features of any other embodiment. All patents and publications discussed herein are incorporated by reference herein in their entirety.

What is claimed is:

1. A method for modifying a heart valve annulus, the method comprising:
   inserting a distal tip of a needle within tissue of a valve annulus, wherein a helical anchor is disposed within a lumen of the needle such that the helical anchor is constrained to a substantially straight state, and wherein the helical anchor is configured to self-transition from the substantially straight state to a natural, coiled state; and
   deploying the helical anchor from the needle and into the tissue of the valve annulus,
   wherein upon deployment from the needle, the helical anchor self-transitions from the substantially straight state to the coiled state to cinch the tissue engaged by the helical anchor.

2. The method of claim 1, further comprising:
   applying RF energy to the helical anchor following the step of deploying the helical anchor.

3. The method of claim 2, wherein the RF energy heats the helical anchor to thereby cause collagen in the tissue to undergo shape change and modify a shape of the valve annulus.

4. The method of claim 1, wherein prior to the step of inserting the distal tip of the needle within tissue of the valve annulus, the method further comprising:
   positioning a distal end of a catheter having the needle loaded within a first lumen thereof adjacent to the valve annulus;
   deploying a clip that is slidably disposed within a second lumen of the catheter into the tissue of the valve annulus to secure the distal end of the catheter relative to the valve annulus; and
   deploying the needle from the distal end of the catheter.

5. The method of claim 1, wherein the step of inserting the distal tip of the needle within tissue of the valve annulus includes capturing a layer of the tissue within a channel defined between a tracking arm of the needle and an outer surface of a distal portion of the needle.

6. The method of claim 1 further comprising:
   percutaneously delivering and inserting a first guide wire into the valve annulus at a first location corresponding with a first commissure of the valve annulus to mark the first location;
   percutaneously delivering and inserting a second guide wire into the valve annulus at a second location corresponding with a mid-point of a posterior aspect of the valve annulus to mark the second location;
   percutaneously delivering and inserting a third guide wire into the valve annulus at a third location corresponding with a second commissure of the valve annulus to mark the third location; and
   thereafter performing the step of inserting the distal tip of the needle within the tissue of the valve annulus to deploy the helical anchor into the tissue of the valve annulus based upon the marked first, second and third locations.

7. The method of claim 1, wherein a push rod is slidably disposed within the lumen of the needle and wherein the step of deploying the helical anchor from the needle and into the tissue of the valve annulus includes withdrawing the needle from around the helical anchor while holding the push rod stationary.

8. The method of claim 1, wherein the helical anchor is formed of a shape-memory material.

9. The method of claim 1, wherein the helical anchor is entirely disposed within a thickness of the valve annulus after deployment.

10. The method of claim 1, wherein the needle is inserted into the tissue to be substantially parallel with a surface of the tissue.

* * * * *